US010266606B2

(12) United States Patent
De Roo et al.

(10) Patent No.: US 10,266,606 B2
(45) Date of Patent: Apr. 23, 2019

(54) METHOD FOR PURIFYING CYS-LINKED ANTIBODY-DRUG CONJUGATES

(71) Applicant: SYNTHON BIOPHARMACEUTICALS B.V., Nijmegen (NL)

(72) Inventors: Guy De Roo, Nijmegen (NL); Ruud Martin Verstegen, Nijmegen (NL); Rudy Gerardus Elisabeth Coumans, Nijmegen (NL)

(73) Assignee: Synthon Biopharmaceuticals B.V., Nijmegen (NL)

( * ) Notice: Subject to any disclaimer, the term of this patent is extended or adjusted under 35 U.S.C. 154(b) by 103 days.

(21) Appl. No.: 15/110,169

(22) PCT Filed: Jan. 9, 2015

(86) PCT No.: PCT/EP2015/050304
§ 371 (c)(1),
(2) Date: Jul. 7, 2016

(87) PCT Pub. No.: WO2015/104359
PCT Pub. Date: Jul. 16, 2015

(65) Prior Publication Data
US 2016/0324979 A1 Nov. 10, 2016

(30) Foreign Application Priority Data
Jan. 10, 2014 (EP) .................................... 14150789

(51) Int. Cl.
C07K 16/32 (2006.01)
A61K 47/68 (2017.01)

(52) U.S. Cl.
CPC .......... C07K 16/32 (2013.01); A61K 47/6803 (2017.08); A61K 47/6851 (2017.08); A61K 47/6889 (2017.08)

(58) Field of Classification Search
None
See application file for complete search history.

(56) References Cited

U.S. PATENT DOCUMENTS

| 4,771,128 A | 9/1988 | Ferris et al. |
| 5,475,092 A | 12/1995 | Chari et al. |
| 5,502,068 A | 3/1996 | Lown et al. |
| 5,579,350 A | 11/1996 | Furukawa et al. |
| 5,585,499 A | 12/1996 | Chari et al. |
| 5,629,430 A | 5/1997 | Terashima et al. |
| 5,646,298 A | 7/1997 | Powell |
| 5,670,492 A | 9/1997 | Amishiro et al. |
| 5,739,350 A | 4/1998 | Kelly et al. |
| 5,843,937 A | 12/1998 | Wang et al. |
| 5,846,545 A | 12/1998 | Chari et al. |
| 7,064,117 B2 | 6/2006 | Denny et al. |
| 7,223,837 B2 | 5/2007 | De Groot et al. |
| 7,705,045 B2 | 4/2010 | De Groot et al. |
| 7,718,688 B2 | 5/2010 | Denny et al. |
| 8,012,978 B2 | 9/2011 | Zhao et al. |
| 8,680,293 B2 | 3/2014 | Beusker et al. |
| 8,889,868 B2 | 11/2014 | Beusker et al. |
| 9,421,278 B2 | 8/2016 | Dokter et al. |
| 9,427,480 B2 | 8/2016 | Santin et al. |
| 9,629,924 B2 | 4/2017 | Beusker et al. |
| 9,815,784 B2 | 11/2017 | Beusker et al. |
| 2003/0050331 A1 | 3/2003 | Ng et al. |
| 2003/0073731 A1 | 4/2003 | Lee |
| 2004/0033962 A1 | 2/2004 | Tietze et al. |
| 2005/0014700 A1 | 1/2005 | Boger |
| 2005/0026987 A1 | 2/2005 | Boger |
| 2005/0148651 A1 | 7/2005 | Denny et al. |
| 2006/0116422 A1 | 6/2006 | De Groot et al. |
| 2006/0233794 A1 | 10/2006 | Law et al. |
| 2007/0037739 A1 | 2/2007 | Wang et al. |
| 2008/0279868 A1 | 11/2008 | Boyd et al. |
| 2008/0311136 A1 | 12/2008 | Beusker et al. |
| 2009/0010945 A1 | 1/2009 | Alley et al. |
| 2009/0111805 A1 | 4/2009 | Morris et al. |
| 2009/0162372 A1 | 6/2009 | King et al. |
| 2009/0318668 A1 | 12/2009 | Beusker et al. |
| 2010/0069617 A1 | 3/2010 | Gagnon |
| 2010/0113476 A1 | 5/2010 | Chen et al. |
| 2011/0065767 A1 | 3/2011 | Beusker et al. |
| 2011/0207767 A1 | 8/2011 | Beusker et al. |
| 2012/0214864 A1 | 8/2012 | Richer et al. |
| 2013/0095172 A1 | 4/2013 | Alavattam et al. |
| 2013/0224227 A1 | 8/2013 | Beusker et al. |
| 2015/0216844 A1 | 8/2015 | Beusker et al. |
| 2016/0008486 A1 | 1/2016 | Dokter et al. |
| 2016/0008487 A1 | 1/2016 | Santin et al. |
| 2016/0052880 A1 | 2/2016 | Beusker et al. |
| 2017/0007717 A1 | 1/2017 | Santin et al. |
| 2017/0014525 A1 | 1/2017 | Dokter et al. |

FOREIGN PATENT DOCUMENTS

| EP | 0263526 A1 | 4/1988 |
| EP | 0154445 B1 | 5/1989 |
| EP | 0656360 A1 | 6/1995 |
| EP | 0702014 A1 | 3/1996 |
| EP | 0359454 B1 | 12/2000 |
| EP | 2380909 A1 | 10/2011 |

(Continued)

OTHER PUBLICATIONS

Schindler et al. (British Journal of Haemotology, 154: 471-476, 2011).*

(Continued)

Primary Examiner — Nelson B Moseley, II
(74) Attorney, Agent, or Firm — Buscher Patent PLLC

(57) ABSTRACT

The present invention relates to a method for purifying a mixture of cysteine-linked antibody-drug conjugates, wherein the amount of non-conjugated antibody is in the range of 0-40% by weight, using hydrophobic interaction chromatography (HIC). The mixture is loaded onto a preparative HIC column using a 0.2-1.5 M aqueous salt solution, in which non-conjugated antibody is collected in a flow-through fraction, followed by elution of a purified mixture of cysteine-linked antibody-drug conjugates using a 0-100 mM aqueous salt solution.

28 Claims, 3 Drawing Sheets

(56) References Cited

FOREIGN PATENT DOCUMENTS

| | | |
|---|---|---|
| JP | H0656697 A | 3/1994 |
| JP | H11500427 A | 1/1999 |
| JP | 2000511893 A | 9/2000 |
| JP | 2004518678 A | 6/2004 |
| JP | 2005532287 A | 10/2005 |
| JP | 2008517905 A | 5/2008 |
| JP | 2008531542 A | 8/2008 |
| JP | 2009529030 A | 8/2009 |
| WO | WO-8804659 A2 | 6/1988 |
| WO | WO-9002746 A1 | 3/1990 |
| WO | WO-9116324 A1 | 10/1991 |
| WO | WO-9531971 A1 | 11/1995 |
| WO | WO-9623497 A1 | 8/1996 |
| WO | WO-9707097 A1 | 2/1997 |
| WO | WO-9712862 A1 | 4/1997 |
| WO | WO-9732850 A1 | 9/1997 |
| WO | WO-9744000 A2 | 11/1997 |
| WO | WO-9745411 A1 | 12/1997 |
| WO | WO-9811101 A2 | 3/1998 |
| WO | WO-9825898 A1 | 6/1998 |
| WO | WO-9825900 A1 | 6/1998 |
| WO | WO-9852925 A1 | 11/1998 |
| WO | WO-9919298 A1 | 4/1999 |
| WO | WO-9931120 A1 | 6/1999 |
| WO | WO-0183448 A2 | 11/2001 |
| WO | WO-0183482 A1 | 11/2001 |
| WO | WO-0230894 A2 | 4/2002 |
| WO | WO-02059122 A1 | 8/2002 |
| WO | WO-02067930 A1 | 9/2002 |
| WO | WO-02067937 A1 | 9/2002 |
| WO | WO-02068412 A1 | 9/2002 |
| WO | WO-02096910 A1 | 12/2002 |
| WO | WO-03022806 A2 | 3/2003 |
| WO | WO-03026577 A2 | 4/2003 |
| WO | WO-03086318 A2 | 10/2003 |
| WO | WO-03097635 A1 | 11/2003 |
| WO | WO-2004032828 A2 | 4/2004 |
| WO | WO-2004069159 A2 | 8/2004 |
| WO | WO-2004069201 A2 | 8/2004 |
| WO | WO-2004101767 A2 | 11/2004 |
| WO | WO-2005032594 A2 | 4/2005 |
| WO | WO-2005079398 A2 | 9/2005 |
| WO | WO-2005084390 A2 | 9/2005 |
| WO | WO-2005103040 A1 | 11/2005 |
| WO | WO-2005105154 A1 | 11/2005 |
| WO | WO-2005112919 A2 | 12/2005 |
| WO | WO-2006002895 A2 | 1/2006 |
| WO | WO-2006012527 A1 | 2/2006 |
| WO | WO-2006037052 A2 | 4/2006 |
| WO | WO-2006043839 A1 | 4/2006 |
| WO | WO-2006110476 A2 | 10/2006 |
| WO | WO-2007038658 A2 | 4/2007 |
| WO | WO-2007051081 A1 | 5/2007 |
| WO | WO-2007059404 A2 | 5/2007 |
| WO | WO-2007089149 A2 | 8/2007 |
| WO | WO-2008074004 A2 | 6/2008 |
| WO | WO-2008083312 A2 | 7/2008 |
| WO | WO-2008103693 A2 | 8/2008 |
| WO | WO-2009017394 A1 | 2/2009 |
| WO | WO-2009026274 A1 | 2/2009 |
| WO | WO-2009064908 A1 | 5/2009 |
| WO | WO-2009064913 A1 | 5/2009 |
| WO | WO-2009073524 A2 | 6/2009 |
| WO | WO-2009073533 A2 | 6/2009 |
| WO | WO-2009073546 A2 | 6/2009 |
| WO | WO-2009134977 A1 | 11/2009 |
| WO | WO-2010027280 A1 | 3/2010 |
| WO | WO-2010033733 A1 | 3/2010 |
| WO | WO-2010062171 A2 | 6/2010 |
| WO | WO 2011/133039 * | 10/2011 ............ A61K 31/43 |
| WO | WO-2011133039 A2 | 10/2011 |
| WO | WO-2012143523 A1 | 10/2012 |
| WO | WO-2013049410 A1 | 4/2013 |
| WO | WO-2013121175 A1 | 8/2013 |
| WO | WO-2015104359 A2 | 7/2015 |
| WO | WO-2015104373 A2 | 7/2015 |
| WO | WO-2015104385 A2 | 7/2015 |

OTHER PUBLICATIONS

Hannblett et al. (Clinical Cancer Research, 10: 7063-7070, 2004, in IDS from Jun. 27, 2017).*

Ouyang (Antibody-Drug Conjugates, Methods in Molecular Biology, 1045: 275-283, 2013, in IDS from Jun. 27, 2017).*

Notice of Allowance dated Oct. 3, 2017 in U.S. Appl. No. 14/174,794, Beusker, P.H. et al., filed Feb. 6, 2014.

Notice of Allowance dated Jun. 29, 2017 in U.S. Appl. No. 14/526,462, Beusker, P.H. et al., filed Oct. 28, 2014.

Final Office Action dated Sep. 20, 2017 in U.S. Appl. No. 15/216,366, Santin, A.D. et al., filed Jul. 21, 2016.

Final Office Action dated Aug. 22, 2017 in U.S. Appl. No. 15/216,407, Dokter, W. et al., filed Jul. 21, 2016.

Amishiro, N., et al., "New Water-soluble Duocarmycin Derivatives: Synthesis and Antitumor Activity of A-Ring Pyrrole Compounds Bearing β-heteroarylacryloyl Groups," Journal of Medicinal Chemistry 42(4):669-676, American Chemical Society, United States (1999).

Amishiro, N., et al., "Synthesis and Antitumor Activity of Duocarmycin Derivatives: A-Ring Pyrrole Compounds bearing β-(5',6',7'-trimethoxy-2'-indolypacryloyl Group," Bioorganic and Medicinal Chemistry 8(7):1637-1643, Elsevier Science, England (2000).

Amsellem-Ouazana, D., et al., "Management of Primary Resistance to Gemcitabine and Cisplatin (G-C) Chemotherapy in Metastatic Bladder Cancer With HER2 Over-Expression," Annals of Oncology 15(3):538, Oxford University Press, England (2004).

Aristoff, P.A. and Johnson, P.D., "Synthesis of CBI-PDE-I-dimer, the Benzannelated Analog of CC-1065," The Journal of Organic Chemistry 57(23):6234-6239, American Chemical Society, United States (1992).

Attard, G., et al., "A Phase Ib Study of Pertuzumab, a Recombinant Humanised Antibody to HER2, and Docetaxel in Patients With Advanced Solid Tumours," British Journal of Cancer 97(10):1338-1343, Nature Publishing Group, England (2007).

Atwell, G.J., et al., "5-Amino-1-(chloromethyl)-1,2-dihydro-3H-benz[e]indoles: Relationships between Structure and Cytotoxicity for Analogues Bearing Different DNA Minor Groove Binding Subunits," Journal of Medicinal Chemistry 42(17):3400-3411, American Chemical Society, United States (1999).

Bagshawe, K.D., et al., "A Cytotoxic Agent can be Generated Selectively at Cancer Sites," British Journal of Cancer 58(6):700-703, Nature Publishing Group on behalf of Cancer Research, England (1988).

Bagshawe, K.D., et al., "Antibody-Directed Enzyme Prodrug Therapy: A Review," Drug Development Research 34(2):220-230, John Wiley & Sons, United States (1995).

Bando, T. and Sugiyama, H., "Synthesis and Biological Properties of Sequence-specific DNA-alkylating Pyrrole-imidazole Polyamides," Accounts of Chemical Research 39(12):935-944, American Chemical Society, United States (2006).

Bartlett, J.M., et al., "Type I Receptor Tyrosine Kinases are Associated with Hormone Escape in Prostate Cancer," The Journal of Pathology 205(4):522-529, John Wiley and Sons, England (2005).

Beckhardt, R.N., et al., "Her-2/*neu* Oncogene Characterization in Head and Neck Squamous Cell Carcinoma," Archives of Otolaryngology-Head & Neck Surgery 121(11):1265-1270, American Medical Association, United States (1995).

Berchuck, A., et al., "Overexpression of *HER-2/neu* is Associated With Poor Survival in Advanced Epithelial Ovarian Cancer," Cancer Research 50(13):4087-4091, American Association for Cancer Research, United States (1990).

Bertotti, A., et al., "A Molecularly Annotated Platform of Patient-derived Xenografts ("Xenopatients") Identifies HER2 as an Effective Therapeutic Target in Cetuximab-resistant Colorectal Cancer," Cancer Discovery 1(6):508-523, American Association for Cancer Research, United States (2011).

(56) References Cited

OTHER PUBLICATIONS

Boger, D.L. and Johnson, D.S., "CC-1065 and the Duocarmycins: Unraveling the Keys to a New Class of Naturally Derived DNA Alkylating Agents," Proceedings of the National Academy of Sciences, USA 92(9):3642-3649, American Association for the Advancement of Science, United States (1995).

Boger, D.L., et al., "CC-1065 and the Duocarmycins: Synthetic Studies," Chemical Reviews 97(3):787-828, American Chemical Society, United States (1997).

Boger, D.L., et al., "Examination of the Role of the Duocarmycin SA Methoxy Substituents: Identification of the Minimum, Fully Potent DNA Binding Subunit," Bioorganic and Medicinal Chemistry Letters 6(18):2207-2210, Elsevier Science, England (1996).

Boger, D.L., et al., "Substituent Effects within the DNA Binding Subunit of CBI Analogues of the Duocarmycins and CC-1065," Bioorganic and Medicinal Chemistry Letters 11(15):2021-2024, Elsevier Science Ltd., England (2001).

Boger, D.L., et al., "Synthesis and Evaluation of a Series of C3-substituted CBI Analogues of CC-1065 and the Duocarmycins," The Journal of Organic Chemistry 66(15):5163-5173, American Chemical Society, United States (2001).

Boger, D.L., et al., "Synthesis and Properties of Substituted CBI Analogs of CC-1065 and the Duocarmycins Incorporating the 7-Methoxy-1,2,9,9a-tetrahydrocyclopropa[c]benz[e]indol-4-one (MCBI) Alkylation Subunit: Magnitude of Electronic Effects on the Functional Reactivity," Journal of Organic Chemistry 61(5):1710-1729, American Chemical Society, United States (1996).

Boyle, K.E., et al., "Synthesis and Evaluation of Duocarmycin SA Analogs Incorporating the Methyl 1,2,8,8a-tetrahydrocyclopropa[c]oxazolo[2,3-e]indol-4-one-6-carboxylate (COI) Alkylation Subunit," Bioorganic and Medicinal Chemistry Letters 20(6):1854-1857, Elsevier Science Ltd., England (2010).

Braga, D., et al., "Crystal Polymorphism and Multiple Crystal Forms" Structure and Bonding 132:25-50 Springer-Verlag, Germany (2009).

Burris, H., and Storniolo, A.M., "Assessing Clinical Benefit in the Treatment of Pancreas Cancer: Gemcitabine Compared to 5-fluorouracil," European Journal of Cancer 33(Suppl. 1):S18-S22, Pergamon Press, England (1997).

Cai, C., et al., "Androgen Receptor Expression in Prostate Cancer Cells is Suppressed by Activation of Epidermal Growth Factor Receptor and ErbB2," Cancer Research 69(12):5202-5209, American Association for Cancer Research, United States (2009).

Calikusu, Z., et al., "The Effect of HER2 Expression on Cisplatin-based Chemotherapy in Advanced Non-small Cell Lung Cancer Patients," Journal of Experimental & Clinical Cancer Research 28:97, BioMed Central, England, 6 pages (2009).

Carter, P., et al., "Identification and Validation of Cell Surface Antigens for Antibody Targeting in Oncology," Endocrine-Related Cancer 11(4):659-687, BioScientifica, England (2004).

Chakravarti, A., et al., "Expression of the Epidermal Growth Factor Receptor and Her-2 Are Predictors of Favorable Outcome and Reduced Complete Response Rates, Respectively, in Patients With Muscle-invading Bladder Cancers Treated by Concurrent Radiation and Cisplatin-based Chemotherapy: a Report From the Radiation Therapy Oncology Group," International Journal of Radiation Oncology, Biology, Physics 62(2):309-317, Elsevier Science Inc, United States (2005).

Chavda, S., et al., "A Novel Achiral seco-cyclopropylpyrido[e]indolone (CPyl) Analog of CC-1065 and the Duocarmycins: Synthesis, DNA Interactions, in Vivo Anticancer and Anti-parasitic Evaluation," Bioorganic and Medicinal Chemistry Letters 18(14):5016-5024, Elsevier Science Ltd., England (2010).

Chen, L., et al., "Dual EGFR/HER2 Inhibition Sensitizes Prostate Cancer Cells to Androgen Withdrawal by Suppressing ErbB3," Clinical Cancer Research 17(19):6218-6228, The Association, United States (2011).

Chevallier, P., et al., "Trastuzumab for Treatment of Refractory/Relapsed HER2-Positive Adult B-ALL: Results of a Phase 2 GRAALL Study," Blood 119(11):2474-2477, American Society of Hematology, United States (2012).

Clark, J.W., et al., "Phase II Trial of 5-Fluororuacil (5-FU), Leucovorin (LV), Oxaliplatin (Ox), and Trastuzamab (T) for Patients With Metastatic Colorectal Cancer (CRC) Refractory to Initial Therapy," Proceedings of the American Society of Clinical Oncology 22:891, Abstract 3584, American Society of Clinical Oncology, United States (2003).

Conroy, T., et al., "FOLFIRINOX versus Gemcitabine for Metastatic Pancreatic Cancer," The New England Journal of Medicine 364(19):1817-1825, Massachusetts Medical Society, United States (2011).

Cumnock, K., et al., "Trisulfide Modification Impacts the Reduction Step in Antibody-drug Conjugation Process," Bioconjugate Chemistry 24(7):1154-1160, American Chemical Society, United States (2013).

Daniell, K., et al., "Design, Synthesis, and Biological Evaluation of Achiral Analogs of Duocarmycin SA," Bioorganic and Medicinal Chemistry Letters 15(1):177-180, Elsevier Science Ltd., England (2005).

Dokter, W., et al., "Novel Her2 Targeting Antibody-Drug Conjugates Based on DNA-Interacting Duocarmycin and an Unique Linker Technology with Great Potential in Breast Cancer and NSCLC," Cancer Research 73(8):Abstract 4329, Proceedings of the 104th Annual Meeting of the American Association for Cancer Research, AACR, United States, Apr. 6-10, 2013, 2 pages.

Dokter, W., et al., "Preclinical Profile of the HER2-Targeting ADC SYD983/SYD985: Introduction of a New Duocarmycin-Based Linker-Drug Platform," Molecular Cancer Therapeutics 13(11):2618-2629, American Association for Cancer Research, United States (Nov. 2014).

Dokter, W.H.A., et al., "In Vitro and in Vivo Antitumor Activity of SYD985, a Novel HER2-Targeting ADC: A Comparison with T-DM1," Cancer Research 74(19):Abstract 2652, Proceedings of the 105th Annual Meeting of the American Association for Cancer Research, Apr. 5-9, 2014, San Diego, CA, 1 page (Oct. 1, 2014).

Duncan, R., "The Dawning Era of Polymer Therapeutics," Nature Reviews Drug Discovery 2(5):347-360, Nature Publisher Group, England (2003).

Ebb, D., et al., "Phase II Trial of Trastuzumab in Combination with Cytotoxic Chemotherapy for Treatment of Metastatic Osteosarcoma With Human Epidermal Growth Factor Receptor 2 Overexpression: A Report From the Children's Oncology Group," Journal of Clinical Oncology 30(20):2545-2551, American Society of Clinical Oncology, United States (2012).

El-Sahwi, K.S., et al., "Development of Targeted Therapy in Uterine Serous Carcinoma, a Biologically Aggressive Variant of Endometrial Cancer," Expert Review of Anticancer Therapy 12(1):41-49, Taylor & Francis, England (2012).

Elvira, C., et al., "Covalent Polymer-Drug Conjugates," Molecules 10(1):114-125, MDPI, c1995, Switzerland (2005).

English, D.P., et al., "T-DM1, A Novel Antibody—Drug Conjugate, is Highly Effective Against Primary HER2 Overexpressing Uterine Serous Carcinoma in Vitro and in Vivo," Cancer Medicine 3(5):1256-1265, John Wiley & Sons Ltd, United States (Jun. 2014).

English Language Translation of WO 98/25900 (cited as document FP79 on accompanying form PTO/SB/08a), Google translate, Apr. 30, 2013, 40 pages.

Extended European Search Report for EP Application No. 14150791.3, European Patent Office, Germany, completed on Jun. 18, 2014, 15 pages.

Fiebig, H-H., et al., "Comparison of Tumor Response in Nude Mice and in the Patients," Behring Institute Mitteilungen 74:343-352, Behringwerke AG, Germany (1984).

Fiebig, H-H., et al., "Gene Signatures Developed from Patient Tumor Explants Grown in Nude Mice to Predict Tumor Response to 11 Cytotoxic Drugs," Cancer Genomics & Proteomics 4(3):197-209, International Institute of Anticancer Research, Greece (2007).

(56) References Cited

OTHER PUBLICATIONS

Fleming, G.F., et al., "Phase II Trial of Trastuzumab in Women with Advanced or Recurrent, HER2-Positive Endometrial Carcinoma: a Gynecologic Oncology Group Study," Gynecologic Oncology 116(1):15-20, Academic Press, United States (2010).

Flygare, J.A., et al., "Antibody-Drug Conjugates for the Treatment of Cancer," Chemical Biology & Drug Design 81(1):113-121, Wiley-Blackwell, England (2013).

Foulkes, W.D., et al., "Triple-Negative Breast Cancer," The New England Journal of Medicine 363:1938-1948, Massachusetts Medical Society, United States (2010).

Frankel, A.E., et al., "Cell Surface Receptor-Targeted Therapy of Acute Myeloid Leukemia: A Review," Cancer Biotherapy Radiopharmaceuticals 15(5):459-476, Mary Ann Liebert, Inc., United States (2000).

Gaborit, N., et al., "Time-Resolved Fluorescence Resonance Energy Transfer (TR-FRET) to Analyze the Disruption of EGFR/HER2 Dimers: A New Method to Evaluate the Efficiency of Targeted Therapy Using Monoclonal Antibodies," The Journal of Biological Chemistry 286(13):11337-11345, American Society for Biochemistry and Molecular Biology, United States (2011).

Garg, K., et al., "Endometrial Carcinoma in Women Aged 40 Years and Younger," Archives of Pathology & Laboratory Medicine 138(3):335-342, American Medical Assn, United States (Mar. 2014).

Gauss, C.M., et al., "Synthesis and Preliminary Evaluation of Duocarmycin Analogues Incorporating the 1,2,11,11a-Tetrahydrocyclopropa[c]naphtho[2,3-e]indol-4-one (CNI) and 1,2,11,11a-Tetrahydrocyclopropa[c]naphtho[1,2-e]indol-4-one (iso-CNI) Alkylation Subunits," Tetrahedron 65(33):6591-6599, Pergamon Press, England (2009).

Gorlick, R., et al., "Expression of HER2/*erb*B-2 Correlates with Survival in Osteosarcoma," Journal of Clinical Oncology 17(9):2781-2788, American Society of Clinical Oncology, United States (1999).

Greenwald, R.B., et al., "A New Aliphatic Amino Prodrug System for the Delivery of Small Molecules and Proteins Utilizing Novel Peg Derivatives," Journal of Medicinal Chemistry 47(3):726-734 American Chemical Society, United States (2004).

Greenwald, R.B., et al., "Effective Drug Delivery by PEGylated Drug Conjugates," Advanced Drug Delivery Reviews 55(2):217-250, Elsevier Science Publishers, B.V., Netherlands (2003).

Hamblett, K.J., et al., "Effects of Drug Loading on the Antitumor Activity of a Monoclonal Antibody Drug Conjugate," Clinical Cancer Research 10(20):7063-7070, American Association for Cancer Research, United States (2004).

Haymarket Media, Inc., "Endometrial Carcinoma Chemotherapy and Other Treatment Regimens," 1 page (revised Mar. 2012).

Hidalgo, M., et al., "A Pilot Clinical Study of Treatment Guided by Personalized Tumorgrafts in Patients with Advanced Cancer," Molecular Cancer Therapeutics 10(8):1311-1316, American Association for Cancer Research, United States (2011).

Hsu, F-N., et al., "The Significance of HER2 on Androgen Receptor Protein Stability in the Transition of Androgen Requirement in Prostate Cancer Cells," American Journal of Physiology. Endocrinology and Metabolism 300(5):E902-E908, American Physiological Society, United States (2011).

Huber B.E., et al., "Retroviral-Mediated Gene Therapy for the Treatment of Hepatocellular Carcinoma: An Innovative Approach for Cancer Therapy," Proceedings of the National Academy of Sciences USA 88(18):8039-8043, National Academy of Sciences, United States (1991).

Hussian, M.H.A., et al., "Trastuzumab, Paclitaxel, Carboplatin, and Gemcitabine in Advanced Human Epidermal Growth Factor Receptor-2/*neu*-Positive Urothelial Carcinoma: Results of a Multicenter Phase II National Cancer Institute Trial," Journal of Clinical Oncology 25(16):2218-2224, American Society of Clinical Oncology, United States (2007).

International Preliminary Report on Patentability for International Application No. PCT/EP2015/050304, The International Bureau of WIPO, Switzerland, dated Jul. 12, 2016, 9 pages.

International Search Report and Written Opinion for International Application No. PCT/EP2015/050304, European Patent Office, Netherlands, dated Jul. 10, 2015, 13 pages.

International Search Report and Written Opinion for International Application No. PCT/EP2015/050332, European Patent Office, Netherlands, dated Jul. 20, 2015, 15 pages.

International Search Report and Written Opinion for International Application No. PCT/EP2015/050350, European Patent Office, Netherlands, dated Jul. 6, 2015, 14 pages.

Irwin, M.E., et al., "Small Molecule ErbB Inhibitors Decrease Proliferative Signaling and Promote Apoptosis in Philadelphia Chromosome-Positive Acute Lymphoblastic Leukemia," PloS One 8(8):e70608, Public Library of Science, United States, 10 pages (2013).

Jeffrey, S.C., et al., "Design, Synthesis, and in Vitro Evaluation of Dipeptide-based Antibody Minor Groove Binder Conjugates," Journal of Medicinal Chemistry 48(5):1344-1358, American Chemical Society, United States (2005).

Jewell, E., et al., "Use of Trastuzumab in the Treatment of Metastatic Endometrial Cancer," International Journal of Gynecological Cancer 16(3):1370-1373, Lippincott Williams & Wilkins, United States (2006).

Kazane, S.A., et al., "Site-Specific DNA-Antibody Conjugates for Specific and Sensitive Immuno-PCR," Proceedings of the National Academy of Sciences of the United States of America 109(10):3731-3736, National Academy of Sciences, United States (2012).

Kelly, R.K., et al., "An Antibody-cytotoxic Conjugate, BIIB015, is a New Targeted Therapy for Cripto Positive Tumours," European Journal of Cancer 47(11):1736-1746, Elsevier Science Ltd., England (2011).

Kingsbury, W.D., et al., "A Novel Peptide Delivery System Involving Peptidase Activated Prodrugs as Antimicrobial Agents. Synthesis and Biological Activity of Peptidyl Derivatives of 5-Fluorouracil," Journal of Medicinal Chemistry 27(11):1447-1451, American Chemical Society, United States (1984).

Kovtun, Y.V. and Goldmacher, V.S., "Cell killing by Antibody—Drug Conjugates," Cancer Letters 255(2):232-240, Elsevier Science Ltd., Ireland (2007).

Kutty, R.V., et al., "Cetuximab Conjugated Vitamine E TPGS Micelles for Targeted Delivery of Docetaxel for Treatment of Triple Negative Breast Cancers," Biomaterials 34(38):10160-10171, Elsevier Science, Netherlands (2013).

Langdon, S.P., et al., "Pertuzumab for the Treatment of Ovarian Cancer," Expert Opinion on Biological Therapy 10(7):1113-1120, Ashley Publications Ltd, England (2010).

Larbouret, C., et al., "In Pancreatic Carcinoma, Dual EGFR/HER2 Targeting with Cetuximab/Trastuzumab is More Effective than Treatment with Trastuzumab/Erlotinib or Lapatinib Alone: Implication of Receptors' Down-regulation and Dimers' Diruption," Neoplasia 14(2):121-130, Stockton Press, United States (2012).

Li, L-S. and Sinha, S.C., "Studies Toward the Duocarmycin Prodrugs for the Antibody Prodrug Therapy Approach," Tetrahedron Letters 50(24):2932-2935, Elsevier, England (2009).

International Preliminary Report on Patentability and Written Option for International Application No. PCT/NL2011/50278, The International Bureau of WIPO, Geneva, Switzerland, dated Oct. 23, 2012, 14 pages.

International Search Report for International Application No. PCT/NL2011/50278, European Patent Office, Riiswijk, Netherlands, dated Feb. 24, 2012, 11 pages.

MacMillan, K.S., et al., "Total Synthesis and Evaluation of *iso*-duocarmycin SA and *iso*-yatakemycin," Journal of the American Chemical Society 131(3):1187-1194, American Chemical Society, United States (2009).

Makhija, S., et al., "Clinical Activity of Gemcitabine Plus Pertuzumab in Platinum-Resistant Ovarian Cancer, Fallopian Tube Cancer, or Primary Peritoneal Cancer," Journal of Clinical Oncology 28(7):1215-1223, American Society of Clinical Oncology, United States (2010).

Mantia-Smaldone, G.M., et al., "Targeted Treatment of Recurrent Platinum-resistant Ovarian Cancer: Current and Emerging Therapies," Cancer Management and Research 3:25-38, Dove Medical Press, New Zealand (2011).

(56) References Cited

OTHER PUBLICATIONS

Mazieres, J., et al., "Lung Cancer That Harbors an *HER2* Mutation: Epidemiologic Characteristics and Therapeutic Perspectives," Journal of Clinical Oncology 31(16):1997-2003, American Society of Clinical Oncology, United States (2013).
McDonagh, C.F., et al., "Engineered Antibody-drug Conjugates with Defined Sites and Stoichiometries of Drug Attachment," Protein Engineering, Design & Selection 19(7):299-307, Oxford University Press, England (2006).
McGovren, J.P., et al, "Preliminary Toxicity Studies with the DNA-Binding Antibiotic, CC-1065," The Journal of Antibiotics 37(1):63-70, Nature Publishing Group, Japan (1984).
Meden, H. and Kuhn, W., "Overexpression of the Oncogene c-erbB-2 (HER2/neu) in Ovarian Cancer: a New Prognostic Factor," European Journal of Obstetrics, Gynecology, and Reproductive Biology 71(2):173-179, Elsevier Scientific Publishers, Ireland (1997).
Mellstedt, H., "Clinical Considerations for Biosimilar Antibodies," EJC Supplements 11(3):1-11, Elsevier Ltd., England (2013).
Melton, R., et al., "The Use of Prodrugs in Targeted Anticancer Therapies," S.T.P. Pharma Sciences 9(1):13-33, Editions de Sank France, France (1999).
Milbank, J.B.J., et al., "Synthesis of 1-Substituted 3-(Chloromethyl)-6-aminoindoline (6-Amino-*seco*-CI) DNA Minor Groove Alkylating Agents and Structure-Activity Relationships for their Cytotoxicity," Journal of Medicinal Chemistry 42(4):649-658, American Chemical Society, United States (1999).
Minner, S., et al., "Low Level Her2 Overexpression Is Associated With Rapid Tumor Cell Proliferation and Poor Prognosis in Prostate Cancer," Clinical Cancer Research 16(5):1553-1560, The American Association of Cancer Research, United States (2010).
Muller, U., "Polymorphism," in Inorganic Structural Chemistry, pp. 14-15, John Wiley & Sons Ltd., England (1993).
Murray, J.L., "Monoclonal Antibody Treatment of Solid Tumors: a Coming of Age," Seminars in Oncology 27(6 Suppl 11):64-70, W.B. Saunders, United States (2000).
National Comprehensive Cancer Network (NCCN), "NCCN Clinical Practice Guidelines in Oncology (NCCN Guidelines) Version 2.2015—Uterine Neoplasms," accessed at http://www.nccn.org/professionals/physician_gls/PDF/uterine.pdf, accessed on Sep. 15, 2015, 85 pages.
Nolting, B., "Linker Technologies for Antibody-Drug Conjugates," Methods in Molecular Biology 1045:71-100, Springer Science+Business Media, LLC, United States (2013).
Ouyang, J., "Drug-to-antibody Ratio (DAR) and Drug Load Distribution by Hydrophobic Interaction Chromatography and Reversed Phase High-performance Liquid Chromatography," Methods in Molecular Biology 1045:275-283, Springer Science+Business Media, LLC, United States (2013).
Parrish, J.P., et al., "Establishment of Substituent Effects in the DNA Binding Subunit of CBI Analogues of the Duocarmycins and CC-1065," Bioorganic and Medicinal Chemistry Letters 11(17):3815-3838, Elsevier Ltd., England (2003).
Parrish, J.P., et al., "Synthesis and Evaluation of N-aryl and N-alkenyl CBI Derivatives," Bioorganic and Medicinal Chemistry Letters 12(22):5845-5856, Elsevier Ltd., England (2004).
Pettit, G.R., et al., "The Dolastatins; 18: Stereospecific Synthesis of Dolaproine," Synthesis 1996(6):719-725, Thieme Medical Publishers, United States (1996).
Popowycz, F., et al., "Synthesis and Reactivity of 4-, 5- and 6-azaindoles," Tetrahedron 63(36):8689-8707, Elsevier Ltd., Netherlands (2007).
Purnell, B., et al., "DNA Interstrand Crosslinking Agents: Synthesis, DNA Interactions, and Cytotoxicity of Dimeric Achiral Seco-amino-CBI and Conjugates of Achiral Seco-amino-CBI with Pyrrolobenzodiazepine (PBD)," Bioorganic and Medicinal Chemistry Letters 16(21):5677-5681, Elsevier Science Ltd., England (2006).
Ramanathan, R.K., et al., "Low Overexpression of HER-2/PPPNeu in Advanced Colorectal Cancer Limits the Usefulness of Trastuzumab (Herceptin®) and Irinotecan as Therapy. A Phase II Trial," Cancer Investigation 22(6):858-865, Marcel Dekker Inc., United States (2004).
Ray-Coquard, I., et al., "HER2 Overexpression/Amplification and Trastuzumab Treatment in Advanced Ovarian Cancer: A GINECO Phase II Study," Clinical Ovarian Cancer 1(1):54-59, Elsevier, The Netherlands (2008).
Ringsdorf, H., "Structure and Properties of Pharmacologically Active Polymers," Journal of Polymer Science: Polymer Symposia 51(1):135-153, John Wiley & Sons, United States (1975).
Robertson, W.M., et al., "Synthesis and Evaluation of a Series of C5'-substituted Duocarmycin SA Analogs," Bioorganic and Medicinal Chemistry Letters 20(9):2722-2725, Elsevier Ltd., England (2010).
Roitt, I.M., "Antigens," in Immunology, 3rd Edition, Roitt, I.M., et al., eds., p. 1.7, Mosby-Year Book Europe Limited, England (1993).
Santin, A.D., et al., "Overexpression of HER-2/Neu in Uterine Serous Papillary Cancer," Clinical Cancer Research 8(5):1271-1279, The Association, United States (2002).
Santin, A.D., et al., "Trastuzumab Treatment in Patients with Advanced or Recurrent Endometrial Carcinoma Overexpressing HER2/neu," International Journal of Gynecology and Obstetrics 102(2):128-131, Elsevier Ireland Ltd., Ireland (2008).
Scholl, S., et al., "Targeting HER2 in Other Tumor Types," Annals of Oncology 12(Suppl 1):581-587, Kluwer Academic Publishers, Netherlands (2001).
Schuster, H.J., et al., "Synthesis of the First Spacer Containing Prodrug of a Duocarmycin Analogue and Determination of its Biological Activity," Organic and Biomolecular Chemistry 8(8):1833-1842, Royal Society of Chemistry, England (2010).
Seo, A.N., et al., "*HER2* Status in Colorectal Cancer: Its Clinical Significance and the Relationship between *HER2* Gene Amplification and Expression," PLoS One 9(5):e98528, Public Library of Science, United States, 9 pages (May 2014).
Shariat, S.F., et al., "Preoperative Plasma HER2 and Epidermal Growth Factor Receptor for Staging and Prognostication in Patients with Clinically Localized Prostate Cancer," Clinical Cancer Research 13(18 Pt 1):5377-5384, The Association, United States (2007).
Shen, B-Q., et al., "Conjugation Site Modulates the in vivo Stability and Therapeutic Activity of Antibody-Drug Conjugates," Nature Biotechnology 30(2):184-189, Nature America Publishing, United States (2012).
Shigematsu, H., et al., "A Case of HER-2-Positive Recurrent Breast Cancer Showing a Clinically Complete Response to Trastuzumab-Containing Chemotherapy After Primary Treatment of Triple-Negative Breast Cancer," World Journal of Surgical Oncology 9:146, Biomed Central Ltd., England (2011).
Slomovitz, B.M., et al., "Her-2/*neu* Overexpression and Amplification in Uterine Papillary Serous Carcinoma," Journal of Clinical Oncology 22(15):3126-3132, American Society of Clinical Oncology, United States (2004).
Sun, M.M.C., et al., "Reduction-Alkylation Strategies for the Modification of Specific Monoclonal Antibody Disulfides," Bioconjugate Chemistry 16(5):1282-1290, American Chemical Society, United States (2005).
Suzawa, T., et al., "Synthesis of a Novel Duocarmycin Derivative DU-257 and its Application to Immunoconjugate Using Poly(ethylene glycol)-dipeptidyl Linker Capable of Tumor Specific Activation," Bioorganic and Medicinal Chemistry 8(8):2175-2184, Elsevier Ltd., England (2000).
Suzuki, M., et al., "*HER2* Gene Mutations in Non-Small Cell Lung Carcinomas: Concurrence with her2 Gene Amplification and her2 Protein Expression and Phosphorylation," Lung Cancer 87(1):14-22, Elsevier Ireland Ltd., Ireland (Jan. 2015).
Synthon, "Synthon Biopharmaceuticals Reports Positive Early Results with its Second Generation HER2-antibody-drug Conjugate," Nijmegen, Netherlands, Jan. 22, 2013, accessed at http://www.synthon.com/en/Corporate/News/PressReleases/Synthon-reports-positive-early-results-with-its-second-generation-HER2-antibody-drug-conjugate.aspx, accessed on Sep. 1, 2015, 3 pages.

(56) References Cited

OTHER PUBLICATIONS

Takezawa, K., et al., "*HER2* Amplification: A Potential Mechanism of Acquired Resistance to EGFR Inhibition in *EGFR*-Mutant Lung Cancers that Lack the Second-Site $EGFR^{T790M}$ Mutation," Cancer Discovery 2(10):922-933, American Association for Cancer Research, United States (2012).

Tichenor, M.S. and Boger, D.L., "Yatakemycin: Total Synthesis, DNA Alkylation, and Biological Properties," Natural Product Reports 25(2):220-226, Royal Society of Chemistry, England (2008).

Tichenor, M.S., et al., "Asymmetric Total Synthesis of (+)- and *ent*-(−)-yatakemycin and Duocarmycin SA: Evaluation of Yatakemycin Key Partial Structures and its Unnatural Enantiomer," Journal of the American Chemical Society 128(49):15683-15696, American Chemical Society, United States (2006).

Tietze, L.F. and Krewer, B., "Novel Analogues of CC-1065 and the Duocarmycins for the Use in Targeted Tumour Therapies," Anticancer Agents in Medicinal Chemistry 9(3):304-325, Bentham Science Publishers Ltd., Netherlands (2009).

Tietze, L.F., et al., "A Strategy for Tumor-Selective Chemotherapy by Enzymatic Liberation of *seco*-Duocarmycin SA-Derivatives from Nontoxic Prodrugs," Bioorganic & Medicinal Chemistry 9(7):1929-1939, Elsevier Science Ltd., England (2001).

Tietze, L.F., et al., "Antitumor Agents: Development of Highly Potent Glycosidic Duocarmycin Analogues for Selective Cancer Therapy," Angewandte Chemie International Edition in English 45(39):6574-6577, Wiley-VCH Verlag GmbH & Co. KGaA, Germany (2006).

Tietze, L.F., et al., "Asymmetric Synthesis and Biological Evaluation of Glycosidic Prodrugs for a Selective Cancer Therapy," ChemMedChem 3(12):1946-1955, Wiley-VCH Verlag GmbH & Co. KGaA, Germany (2008).

Tietze, L.F., et al., "Determination of the Biological Activity and Structure Activity Relationships of Drugs Based on the Highly Cytotoxic Duocarmycins and CC-1065," Toxins 1(2):134-150, MDPI AG, Switzerland (2009).

Tietze, L.F., et al., "Selective Treatment of Cancer: Synthesis, Biological Evaluation and Structural Elucidation of Novel Analogues of the Antibiotic CC-1065 and the Duocarmycins," Chemistry A European Journal 13(16):4396-4409, Wiley-VCH Verlag GmbH & Co. KGaA, Germany (2007).

Tietze, L.F., et al., "Glycosidic Prodrugs of Highly Potent Bifunctional Duocarmycin Derivatives for Selective Treatment of Cancer," Angewandte Chemie (International Edition in English) 49(40):7336-7339, Wiley-VCH Verlag GmbH & Co. KGaA, Germany (2010).

Tietze, L.F., et al., "Highly Selective Glycosylated Prodrugs of Cytostatic CC-1065 Analogues for Antibody-Directed Enzyme Tumor Therapy," Chembiochem 2(10):758-765, Wiley-VCH Verlag GmbH & Co. KGaA, Germany (2001).

Tietze, L.F., et al, "Synthesis and Biological Evaluation of Novel Analogues and Prodrugs of the Cytotoxic Antibiotic CC-1065 for Selective Cancer Therapy," European Journal of Organic Chemistry 10:1634-1645, Wiley-VCH Verlag GmbH & Co. KGaA, Germany (2002).

Tietze, L.F., et al., "Synthesis of a Novel Pentagastrin-Drug Conjugate for a Targeted Tumor Therapy," Chemistry a European Journal 14(9):2811-2818, Wiley-VCH Verlag GmbH & Co. KGaA, Germany (2008).

Toki, B.E., et al., "Protease-Mediated Fragmentation of p-Amidobenzyl Ethers: A New Strategy for the Activation of Anticancer Prodrugs," The Journal of Organic Chemistry 67(6):1866-1872, American Chemical Society, United States (2002).

Trail, P.A., "Antibody Drug Conjugates as Cancer Therapeutics," Antibodies 2:113-129, MDPI AG, Switzerland (2013).

Tsai, C.-M., et al., "Correlation of Intrinsic Chemoresistance of Non-Small-Cell Lung Cancer Cell Lines with HER-2/neu Gene Expression but not with ras Gene Mutations," Journal of the National Cancer Institute 85(11):897-901, Oxford University Press, England (1993).

Van Der Lee, M., et al., "Poster 2652: The HER2-targeting ADC SYD985 Shows Superior Antitumor Activity Compared to T-DM1 in Preclinical Studies with an Activity Profile that Includes Low-HER2 Expressing Breast Cancers," AACR Annual Meeting 2014, Apr. 5-9, 2014, San Diego, CA, 1 page.

Van Der Lee, M.M.C., et al., "The Preclinical Profile of the Duocarmycin-Based HER2-Targeting ADC SYD985 Predicts for Clinical Benefit in Low HER2-Expressing Breast Cancers," Molecular Cancer Therapeutics 14(3):692-703, American Association for Cancer Research, United States (Mar. 2015).

Verheijden, G., et al., "Poster 850294: Preclinical Data of SYD985 Support the Clinical Investigation of this Novel Anti-HER2 Antibody-Drug Conjugate in Breast Cancer Patients with Low Levels of HER2 Expression," 2014 San Antonio Breast Cancer Symposium, Dec. 2014, 1 page.

Vippagunta, S.R., et al., "Crystalline Solids," Advanced Drug Delivery Reviews 48(1):3-26, Elsevier Science B.V., Netherlands (2001).

Wang, Y., et al., "CC-1065 Analogues Bearing Different Dna-binding Subunits: Synthesis, Antitumor Activity, and Preliminary Toxicity Study," Journal of Medicinal Chemistry 46(4):634- 637, American Chemical Society, United States (2003).

Wang, Y., et al., "Design, Synthesis, Cytotoxic Properties and Preliminary DNA Sequencing Evaluation of CPI—N-methylpyrrole Hybrids. Enhancing Effect of a *trans* Double Bond Linker and Role of the Terminal Amide Functionality on Cytotoxic Potency," Anticancer Drug Design 11(1):15-34, Oxford University Press, United States (1996).

Wang, Y., et al., "Synthesis and Antitumor Activity of CBI-bearing Ester and Carbamate Prodrugs of CC-1065 Analogue," Bioorganic and Medicinal Chemistry Letters 14(23):7854-7861, Elsevier Ltd., England (2006).

Wang, Y., et al., "Synthesis and Preliminary Biological Evaluations of CC-1065 Analogues: Effects of Different Linkers and Terminal Amides on Biological Activity," Journal of Medicinal Chemistry 43(8):1541-1549, American Chemical Society, United States (2000).

Website: Champions Oncology, "Predictive value," accessed at http://web.archive.org/web/20111204221017/http:/www.championsoncology.com/translationaloncologysolutions/predictivevalue, accessed on Oct. 9, 2015, 2 pages.

Wrasidlo, W., et al., "Induction of Endonucleolytic DNA Fragmentation and Apoptosis by the Duocarmycins," Bioorganic & Medicinal Chemistry Letters 4(4):631-636, Elsevier Science Ltd., Great Britain (1994).

Non-Final Office Action dated Oct. 24, 2012, in U.S. Appl. No. 12/671,609, Beusker, P.H. et al., filed Oct. 26, 2010.

Final Office Action dated May 8, 2013, in U.S. Appl. No. 12/671,609, Beusker, P.H. et al., filed Oct. 26, 2010.

Notice of Allowance dated Nov. 6, 2013, in U.S. Appl. No. 12/671,609, Beusker, P.H. et al., filed Oct. 26, 2010.

Non-Final Office Action dated Apr. 22, 2013, in U.S. Appl. No. 13/126,920, Beusker, P.H. et al., filed Apr. 29, 2011.

Final Office Action dated Jan. 7, 2014, in U.S. Appl. No. 13/126,920, Beusker, P.H. et al., filed Apr. 29, 2011.

Notice of Allowance dated Jul. 7, 2014, in U.S. Appl. No. 13/126,920, Beusker, P.H. et al., filed Apr. 29, 2011.

Non-Final Office Action dated Mar. 20, 2015, in U.S. Appl. No. 13/642,847, Beusker, P.H. et al., filed Nov. 27, 2012.

Final Office Action dated Dec. 2, 2015, in U.S. Appl. No. 13/642,847, Beusker, P.H. et al., filed Nov. 27, 2012.

Non-Final Office Action dated Jun. 2, 2016 in U.S. Appl. No. 13/642,847, Beusker, P.H. et al., § 371(c) dated Nov. 27, 2012.

Notice of Allowance dated Jan. 11, 2017 in U.S. Appl. No. 13/642,847, Beusker, P.H. et al., § 371(c) dated Nov. 27, 2012.

Non-Final Office Action dated Dec. 18, 2015, in U.S. Appl. No. 14/174,794, Beusker, P.H. et al., filed Feb. 6, 2014.

Final Office Action dated Jul. 27, 2016 in U.S. Appl. No. 14/174,794, Beusker, P.H. et al., filed Feb. 6, 2014.

Non-Final Office Action dated Jun. 2, 2016 in U.S. Appl. No. 14/526,462, Beusker, P.H. et al., filed Oct. 28, 2014.

Final Office Action dated Jan. 13, 2017 in U.S. Appl. No. 14/526,462, Beusker, P.H. et al., filed Oct. 28, 2014.

(56) References Cited

OTHER PUBLICATIONS

Non-Final Office Action dated Mar. 16, 2016 in U.S. Appl. No. 14/859,201, Dokter, W. et al., filed Sep. 18, 2015.
Notice of Allowance dated Jun. 30, 2016 in U.S. Appl. No. 14/859,201, Dokter, W. et al., filed Sep. 18, 2015.
Non-Final Office Action dated Mar. 9, 2016 in U.S. Appl. No. 14/859,221, Santin, A.D. et al., filed Sep. 18, 2015.
Notice of Allowance dated Jun. 29, 2016 in U.S. Appl. No. 14/859,221, Santin, A.D. et al., filed Sep. 18, 2015.
Non-Final Office Action dated Nov. 22, 2016 in U.S. Appl. No. 15/216,366, Santin, A.D. et al., filed Jul. 21, 2016.
Non-Final Office Action dated Oct. 21, 2016 in U.S. Appl. No. 15/216,407, Dokter, W. et al., filed Jul. 21, 2016.
Non-Final Office Action dated May 4, 2017 in U.S. Appl. No. 14/174,794, Beusker, P.H. et al., filed Feb. 6, 2014.

\* cited by examiner

A. Mixture of cysteine-linked antibody-drug conjugates according to formula (II) before HIC purification B. HIC eluate after purification according to Example 3.

A. Mixture of cysteine-linked antibody-drug conjugates according to formula (II) before HIC purification

B. HIC eluate after purification according to Example 4.

US 10,266,606 B2

METHOD FOR PURIFYING CYS-LINKED ANTIBODY-DRUG CONJUGATES

FIELD OF THE INVENTION

The present invention relates to a method for purifying a mixture of cysteine (Cys)-linked antibody-drug conjugates (ADCs), in particular of a mixture wherein the amount of non-conjugated antibody is in the range of 10-40% by weight.

Such Cys-linked ADCs may have an important role in new targeted cancer treatments. Therefore, having an industrial (preparative) scale method for purifying a mixture of Cys-linked ADCs is a key requirement for the future commercial success of such ADCs.

BACKGROUND OF THE INVENTION

In recent years, dozens of ADCs have been taken into preclinical and clinical development and two ADCs have been approved for marketing in the last couple of years. Apart from more recent developments for conjugating linker-drugs to (monoclonal) antibodies (mAbs), the drug in most of the ADCs in (pre)clinical development and in the two currently marketed ADCs is either linked to the antibody through the N-atom of a lysine residue or through the S-atom of a cysteine residue. The marketed product Kadcyla® or ado-trastuzumab emtansine (Roche/Genentech ImmunoGen) is an example of a lysine-linked ADC and Adcetris® or brentuximab vedotin (Seattle Genetics/Takeda Millennium) is an example of a cysteine-linked ADC. One of the ADCs currently in (pre)clinical development is a cysteine-linked ADC of formula (II) shown herein below in which a duocarmycin drug is conjugated through a cysteine residue to trastuzumab.

Duocarmycins, first isolated from a culture broth of *Streptomyces* species, are members of a family of antitumor antibiotics that include duocarmycin A, duocarmycin SA, and CC-1065. These extremely potent agents allegedly derive their biological activity from an ability to sequence-selectively alkylate DNA at the N3 position of adenine in the minor groove, which initiates a cascade of events that terminates in an apoptotic cell death mechanism.

In order to make Cys-linked ADCs, the antibody typically is partially reduced to convert one or more interchain disulfide bonds into two or more free cysteine residues. The thiol or sulfhydryl (SH) groups of the free cysteine residues are then subsequently conjugated with a linker-drug molecule to form a Cys-linked ADC. Typically, this conjugation process gives a random, heterogeneous mixture of antibodies loaded with 0, 2, 4, 6 and 8 linker-drugs. The lower is the average drug-to-antibody ratio (DAR), the higher is the amount of non-conjugated antibody (DAR0) in the reaction mixture.

Drug loading is known to have an effect on the antitumor activity of the ADC as described for example by K. J. Hamblett et al. in Clinical Cancer Research 10 (2004) 7063-7070. It also affects CMC (Chemistry, Manufacturing and Control) properties like aggregation.

WO2011/133039 of Applicant discloses a series of novel analogs of the DNA-alkylating agent CC-1065 and antibody-drug conjugates (ADCs) thereof. In Example 15, the preparation of a number of trastuzumab-duocarmycin conjugates has been described using 1.1 molar equivalents of a reducing agent to generate 2 free thiol groups per mAb. After quenching, the ADCs were purified using an r-Protein A column to give linker-drug conjugates having an average DAR of approx. 2.

The prior art discloses the use of hydrophobic interaction chromatography (HIC) as a polishing step in many monoclonal antibody (mAb) purification processes. It is mentioned that this mode of chromatography is particularly useful for aggregate removal, and it provides good clearance of other process-related impurities such as host cell protein(s), DNA, endotoxins, leached Protein A and endogenous viruses.

HIC is also a well-established method for the (analytical) determination of the DAR and drug load distribution for cysteine-linked ADCs (Laurent Ducry (ed.), Antibody-Drug Conjugates, Methods in Molecular Biology, 1045 (2013) 275-283). Chapter 17 of this book by Jun Ouyang depicts in FIG. 2 on page 276 a representative HIC chromatogram of a Cys-linked ADC (i.e., MC-VC-PABC-MMAE). It is mentioned that elution with a gradient of a decreasing salt concentration and an increasing organic modifier impacts the column retention of the drug-loaded species with the least hydrophobic, unconjugated form (i.e. non-conjugated antibody, DAR0) eluting first, and the most hydrophobic antibody with 8 linker-drugs (DAR8) eluting last. The data in Table 2 on page 279 show that with a weighted average DAR of 3.6 the mixture of Cys-linked ADCs only contains 4.7% of non-conjugated antibody.

U.S. Pat. No. 4,771,128 describes a method for isolating and purifying toxin conjugates using HIC, in particular for immunoglobulin (antibody) conjugated to the toxic ribosome-inactivating protein ricin A. The method involves first removing unconjugated ricin A and aggregates via sizing chromatography (i.e., size exclusion chromatography, SEC), followed by hydrophobic gel chromatography (i.e., HIC, using Phenyl Sepharose CL-4B, volume 70 ml), in which the conjugate mixture was separated by eluting with salt solutions of decreasing ionic strength. The non-conjugated immunoglobulin was eluted first. The buffer used in both the sizing step and the subsequent chromatographic separation step contained sodium chloride (1 M) at a flow rate of about 20-40 ml/h, cf. Example 1. In an alternative embodiment, a "fast flow" chromatographic separation and purification is provided (i.e., using Phenyl Sepharose CL-4B, column diameter 1 cm, volume 3.14 ml) wherein the unconjugated immunoglobulin is removed with the first column volume of phosphate buffer/sodium chloride (1.5 M) solution at a flow rate of about 0.13 ml/h, cf. Example 2, and the immunoconjugate is removed with a second column volume of phosphate buffer containing 10-60 vol. % of an organic solvent (i.e., 60 vol. % glycerol in Example 2).

The main disadvantage of the methods disclosed in the prior art is the use of an organic solvent which is neither desirable nor acceptable for an industrial scale process.

A problem that has not been addressed in the prior art to the best of Applicant's knowledge is the scaling up of the ADC purification process.

Having reviewed the prior art, there is clearly a need for a new method for purifying mixtures of Cys-linked ADCs. In particular, it would be desirable to have a method for the purification of mixtures of Cys-linked ADCs having an average DAR of about 2-3, which typically contain a relatively high amount of non-conjugated antibody, sometimes as much as 40% by weight, on an industrial preparative scale, and not having to use multiple chromatographic steps.

SUMMARY OF THE INVENTION

The present invention relates to a new method for the purification of a mixture of cysteine-linked antibody-drug conjugates, in particular of a mixture having an average DAR of about 2-3 wherein the amount of non-conjugated antibody is in the range of 10-40% by weight.

In a first aspect, the present invention provides for a method for purifying a mixture of cysteine-linked antibody-drug conjugates, wherein the amount of non-conjugated antibody is in the range of 10-40% by weight comprising:
a. providing the mixture in a 0.2-1.5 M aqueous salt solution;
b. loading said solution onto a preparative hydrophobic interaction chromatography column;
c. collecting a flow-through fraction that contains non-conjugated antibody;
d. washing said column with a 0.2-1.5 M aqueous salt solution while collecting the flow-through fraction; and
e. eluting said column with a 0-100 mM aqueous salt solution to obtain a purified mixture of cysteine-linked antibody-drug conjugates.

In a particularly preferred embodiment of the present invention, the mixture of cysteine-linked antibody-drug conjugates is of the formula (II)

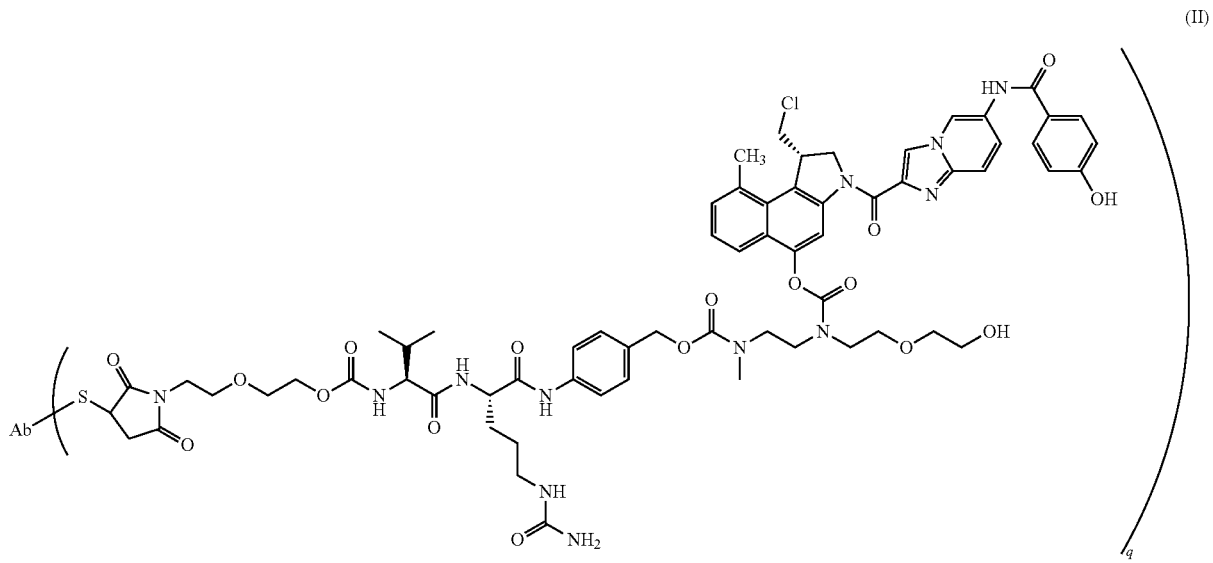

(II)

wherein
Ab is trastuzumab, and
q ranges from 0 to 8.

DETAILED DESCRIPTION OF THE INVENTION

Figure 1:
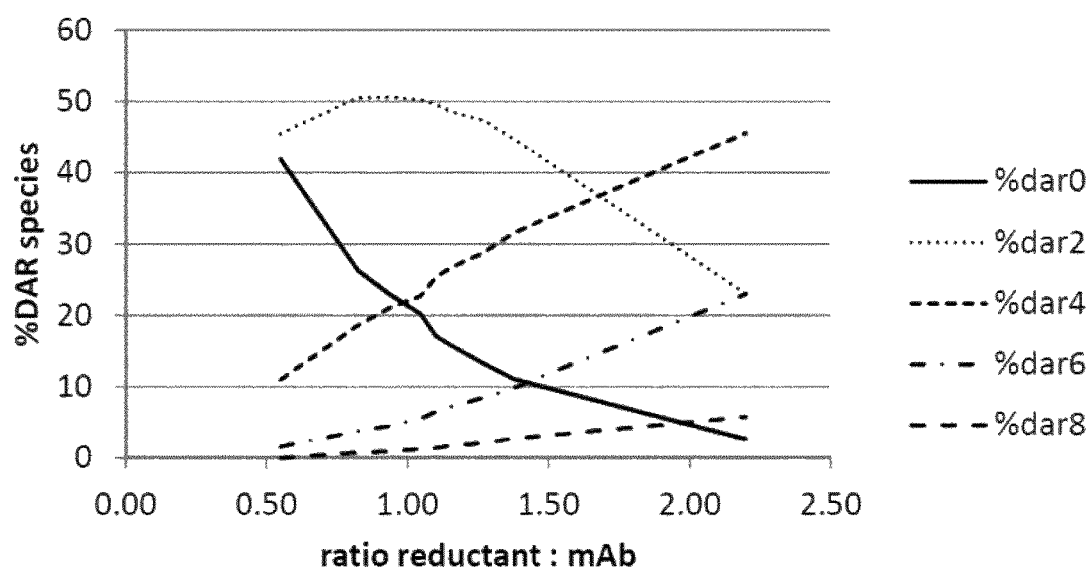
FIG. 1 shows an example of the influence of the amount of reductant on the distribution of DAR species. When using 1.0 equivalent of reductant, the percentage of non-conjugated trastuzumab antibody DAR0 is about 20% by weight.

In accordance with the present invention, it was found that a mixture of cysteine-linked antibody-drug conjugates (Cys-linked ADCs) wherein the amount of non-conjugated antibody is in the range of 10-40% by weight may be advantageously purified from non-conjugated antibody (DAR0) and non-conjugated linker-drug, which typically is quenched after completion of the conjugation reaction, by hydrophobic interaction chromatography. The method according to the present invention comprises:
a. providing the mixture in a 0.2-1.5 M aqueous salt solution;
b. loading said solution onto a preparative hydrophobic interaction chromatography column;
c. collecting a flow-through fraction that contains non-conjugated antibody;
d. washing said column with a 0.2-1.5 M aqueous salt solution while collecting the flow-through fraction; and
e. eluting said column with a 0-100 mM aqueous salt solution to obtain a purified mixture of cysteine-linked antibody-drug conjugates.

In the context of the present specification with "salt" is not meant a "buffer" (salt). Examples of suitable salts and buffers to be used in accordance with the method of the present invention are given herein below. Advantageously, in the method of the present invention buffered aqueous salt solutions are used.

In accordance with the method of the present invention, only aqueous solutions are used, hence, no added organic solvent is used in either step a, b, d or e. To be clear, step e can be carried out in the absence of salt.

The claimed method involves contacting a mixture of Cys-linked ADCs with HIC column packing material in an aqueous salt solution under column loading conditions that permit the mixture of antibodies loaded with 2 to 8 linker-drugs, the non-conjugated linker-drug and impurities, typically aggregates, to bind to the column packing material, while the non-conjugated antibody does not bind and immediately is washed off/flows through the column under loading conditions. Elution with a lower concentration of the aqueous salt solution will separate the Cys-linked ADCs from the non-conjugated linker-drug and impurities which remain bound to the column packing material/stay on the column.

The aqueous salt solution used for loading (step b) and washing (step d) can be the same or different. Advantageously, the aqueous salt solution used for loading (step b) and washing (step d) is the same.

As is known to the person skilled in the art, and as described in paragraph [0057] of US20100069617, optimal loading/binding and elution conditions on a HIC column depend on a number of factors. Therefore, variation in the individual retention characteristics of different mixtures of ADCs, e.g., due to variations in antibody, linker and drug, makes it desirable to customize/optimize the operating conditions of the HIC column in accordance with the present invention. This optimization primarily involves determining the hydrophobicity of the mixture of ADCs which is to be purified, e.g., by determining the (relative) hydrophobicity of the DAR2 species of any specific ADC, and selecting the (hydrophobicity of the) column packing material. It further involves choosing/optimizing the loading/binding aqueous salt concentration, the eluting aqueous salt concentration, the concentration of any buffering salt, and the pH.

Mixtures of Cys-linked ADCs of the formulae (I) and (II) in accordance with the present invention have the linker-drug conjugated to the antibody through the S-atom of a cysteine residue, i.e., they are cysteine-linked antibody-drug conjugates. Typically, the cysteine residue is a natural cysteine residue which is present in the heavy and/or light chain of the antibody (Ab) and forms interchain disulfide bonds. The present invention is particularly drawn to the purification of ADC compounds wherein the linker-drug is conjugated through interchain disulfide bonds of Abs, more particularly mAbs. For example, IgG1 antibodies typically have four interchain disulfide bonds, all four located in the hinge region of antibodies, and after (partial) reduction of the disulfide bonds the linker-drug is randomly attached to free thiol groups.

Mixtures of Cys-linked ADC compounds of the formulae (I) and (II) in accordance with the present invention can be obtained according to methods and procedures that are well known to a person skilled in the art. Conjugation through interchain disulfide bonds can occur after complete or partial reduction of said disulfide bonds. Suitable methods for preparing such compounds can be found in the description and examples of Applicant's WO2011/133039. In particular, Example 15 of WO2011/133039 describes the partial reduction of trastuzumab to generate 2 free thiol groups per mAb and conjugation with a number of linker-drugs to ADCs having an average DAR of approx. 2. Examples 7 and 8 of WO2005/084390 describe partial reduction, partial reduction/partial reoxidation, and complete reduction strategies for (partial) loading of antibodies with the linker-drug vcM-MAE.

The mixture of cysteine-linked antibody-drug conjugates (Cys-linked ADCs) to be purified in accordance with the present invention contains an amount of non-conjugated antibody in the range of 10-40% by weight, more particularly in the range of 10-35% by weight, even more particularly in the range of 15-35% by weight. It is well-known in the art that the amount of non-conjugated antibody present after conjugation decreases with increasing average drug-to-antibody ratio (DAR). As an example, the present inventors have found that when using more than 1.5 equivalents of a reducing agent to reduce the interchain disulfide bridges of the monoclonal antibody trastuzumab, less than 10% by weight of non-conjugated antibody (DAR0) is present in the mixture of conjugates. When using 1.0 equivalent of a reducing agent, a maximum amount of approx. 50% by weight of DAR2 is present in the mixture of conjugates and the percentage of non-conjugated antibody (DAR0) trastuzumab is about 20% by weight (see FIG. 1). It is to be noted that the distribution of DAR species with the ratio of reductant:mAb varies depending on the reactants and reaction conditions used.

The method in accordance with the present invention is particularly advantageous when striving to have an average DAR of about 2-3, more particularly of from 2.6 to 2.9, even more particularly of from 2.7 to 2.9.

The preparative HIC column to be used in accordance with the method of the present invention can be any preparative column which is commercially available. Examples of suppliers of such columns and/or of suitable column packing materials include Tosoh Bioscience, GE Healthcare, Bio-Rad and Merck Millipore.

Said HIC column can be packed with Fractogel EMD propyl (Merck), Fractogel EMD phenyl (Merck Millipore), Butyl-S sepharose (GE Healthcare), Octyl Sepharose (GE Healthcare), Capto Octyl (GE Healthcare), Capto Butyl (GE Healthcare), Capto Phenyl ImpRes (GE Healthcare), Capto Butyl ImpRes (GE Healthcare), Toyopearl PPG-600M (Tosoh Bioscience), Toyopearl Hexyl-650 (Tosoh Bioscience), Toyopearl Butyl-650 (Tosoh Bioscience), Toyopearl Phenyl-650 (Tosoh Bioscience), Toyopearl Ether-650 (Tosoh Bioscience), Macroprep t-Butyl (Bio-Rad), Macroprep phenyl (Bio-Rad), Cellufine Butyl (JNC Corporation), Cellufine Phenyl (JNC Corporation) or Poros HP2 (Applied Biosystems).

Advantageously, said HIC column is packed with GE Healthcare's resins Butyl-S Sepharose 6 Fast Flow (FF), Capto Octyl, Octyl Sepharose 4 Fast Flow, Phenyl Sepharose 6 Fast Flow, Capto Butyl, Butyl Sepharose 4 Fast Flow or Capto Butyl ImpRes, or Tosoh Bioscience's resin Toyopearl PPG-600M. The relative hydrophobicity and many other characteristics of the various column packing materials/resins can be derived from information leaflets on said resins which can be obtained from the suppliers. Preferably, in accordance with the method of the present invention, the HIC column is packed with Butyl-S Sepharose 6 FF, Capto Butyl, Butyl Sepharose 4 FF, Capto Butyl ImpRes or Toyopearl PPG-600M, more preferably it is packed with Butyl Sepharose 4 FF, Capto Butyl ImpRes or Toyopearl PPG-600M, most preferably it is packed with Butyl Sepharose 4 FF or Toyopearl PPG-600M.

Typically, in accordance with the method of the present invention, the column bed height is about 20-25 cm, advantageously about 20 cm, and the pressure on the column is kept below 2 bar.

The column dimensions are dictated by the amount of ADC material that one desires or needs to load onto the HIC column. As is well known to the person skilled in the art, the amount of ADC material that can be loaded increases with column internal diameter and column length.

The preparative HIC column to be used in accordance with the method of the present invention typically has a diameter in the range of 4.0-2,000 mm, preferably 15-2,000 mm, more preferably 80-2,000 mm, most preferably 400-2,000 mm. The larger the diameter of the column, the more ADC material can be loaded onto the top of the column. Advantageously, because the column loading and washing conditions are so-chosen that the non-conjugated antibody (DAR0) flows through the column, the capacity of the column increases. For example, if the amount of non-conjugated antibody present in the mixture of Cys-linked ADCs is 30% by weight, the purification process in accordance with the present invention allows for an approximate 30% higher loading of said column.

The amount of ADC material that is loaded on the preparative column used in accordance with the method of the present invention typically is in the range of 5-50 g/L, preferably in the range of 5-40 g/L, more preferably 10-40 g/L, even more preferably 30-40 g/L of column packing material.

In accordance with the method of the present invention, advantageously batch amounts of from 20 to 2,000 g can be purified, making the presently claimed HIC purification process suitable for an industrial scale production of GMP (Good Manufacturing Practice) ADC material.

Apart from the column diameter and length, also the average particle size ($d_{50,volume}$, median particle size of the cumulative volume distribution) of the column packing material is of relevance.

In accordance with the method of the present invention, the particle size chosen allows for a good separation at a minimal flow rate. In accordance with the method of the present invention the column packing material has a particle size in the range of 30-180 μm. Preferably, the column packing material has a particle size in the range of 35-100 μm; even more preferably, the column packing material has a particle size in the range of 45-90 μm.

In accordance with the method of the present invention, the flow rate is in the range of 50-300 cm/h. Preferably, the flow rate is in the range of 80-250 cm/h, more preferably 100-220 cm/h, most preferably about 100-110 cm/h.

In accordance with the method of the present invention, the elution in step e is either performed in a regular mode (i.e., flow during elution is in the same direction as flow during loading and washing) or in a reverse mode (i.e., flow during elution is in the opposite direction as flow during loading and washing). The reverse-mode elution of the purified mixture of Cys-linked ADCs is particularly advantageous in case the (conjugation reaction) mixture of ADCs is purified from unconjugated linker-drug, e.g., by subjecting said (conjugation reaction) mixture to (e.g., activated carbon) filtration before applying the claimed method of purification.

Advantageously, the salt of the aqueous salt solution is selected from the group consisting of potassium thiocyanate, sodium chloride, potassium chloride, ammonium chloride, sodium sulphate, potassium sulphate and ammonium sulphate. Preferably, the salt is sodium chloride or ammonium sulphate. More preferably, the salt is ammonium sulphate.

In accordance with the method of the present invention, the salt of the aqueous salt solution for loading (step b) and washing (step d) may be the same or different from the salt of the aqueous salt solution for eluting (step e). Advantageously, the same salt is used for steps b, d and e.

In accordance with the method of the present invention, the aqueous salt solution for loading (step b) and washing the column (step d) has a concentration of 0.2-1.5 M. Preferably, the aqueous salt solution has a concentration of 0.2-1.0 M, more preferably 0.45-0.9 M, most preferably 0.55-0.9 M.

In accordance with the method of the present invention, the aqueous salt solution for eluting the column (step e) has a concentration of 0-100 mM. Preferably, the aqueous salt solution has a concentration of 0-90 mM, more preferably 0-80 mM, even more preferably 0-70 mM, most preferably 0-55 mM.

In accordance with the method of the present invention, preferably the aqueous salt solution further contains a buffer. Advantageously, when the aqueous salt solution has a concentration of 0 mM (step e), it contains a buffer. Advantageously, the buffer is selected from the group consisting of sodium phosphate, potassium phosphate, ammonium phosphate, sodium acetate, potassium acetate, sodium citrate, potassium citrate, ammonium citrate and mixtures thereof. Preferably, the buffer is a phosphate, acetate or citrate or a mixture thereof such as a citrate-phosphate buffer. More preferably, the buffer is sodium phosphate or sodium acetate.

In accordance with the method of the present invention, the buffer for loading (step b), washing (step d) and eluting the column (step e) has a concentration of 0-100 mM, preferably 0-50 mM, more preferably 20-30 mM. Advantageously, a buffered aqueous salt solution is used in all steps (step a to e) of the method of the present invention.

The buffered aqueous salt solution that is advantageously used in accordance with the method of the present invention preferably is buffered to a pH of from about 4 to about 8, more preferably from about 5 to about 7, most preferably from about 5.0 to about 5.5.

Hydrophobic interaction chromatography of ADCs in accordance with the method of the present invention makes use of differences in hydrophobic properties of non-conjugated antibodies, antibodies loaded with up to 8 linker-drugs, non-conjugated linker-drug and impurities, i.e., aggregates, in order to achieve separation and isolation of a purified mixture of Cys-linked ADCs. The more hydrophobic is the antibody, ADC, linker-drug or impurity, the stronger it will interact with the column packing material.

In accordance with the method of the present invention, the hydrophobicity of the desired ADC comprised in the mixture of cysteine-linked antibody-drug conjugates is measured by determining the retention time on an analytical HIC column relative to a reference, i.e., the retention time of commercially available mAb trastuzumab (Herceptin®, Roche/Genentech). To measure the hydrophobicity, an ADC sample is prepared having a final concentration of 1 mg/mL of cysteine-linked antibody-drug conjugates in 0.8 M ammonium sulphate and the analytical HIC column used is a TSKgel Butyl-NPR column (Tosoh Bioscience). The ADC sample is eluted using a linear gradient from 100% Buffer C (25 mM sodium phosphate, 1.5 M ammonium sulphate, pH 6.95) to 100% Buffer D (25 mM sodium phosphate, pH 6.95, 20% isopropanol) at 0.4 ml/min over 20 minutes and the retention time of the DAR2 species in the ADC sample is measured at 214 nm absorbance relative to trastuzumab (Herceptin®).

In accordance with the method of the present invention, using the analytical HIC column and method described in the previous paragraph, the DAR2 Cys-linked ADC species has a relative hydrophobicity in the range of 0.1-0.6, particularly 0.2-0.5, more particularly 0.2-0.45, trastuzumab (Herceptin®) having a retention time (Rt) of 6.7 minutes.

The method according to the present invention is particularly suitable for the purification of a mixture of cysteine-linked antibody-drug conjugates of the formula (I)

(I)
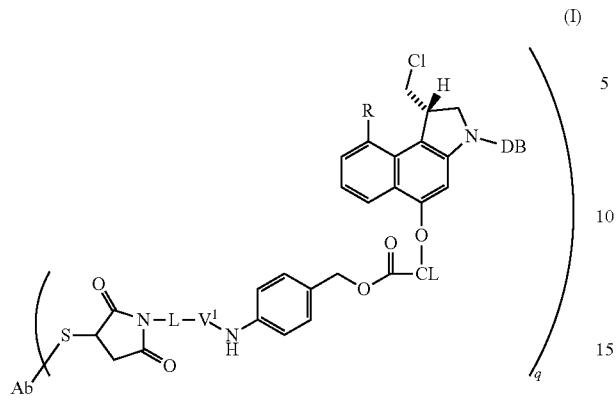
wherein
Ab is an antibody,
L is a linking group selected from
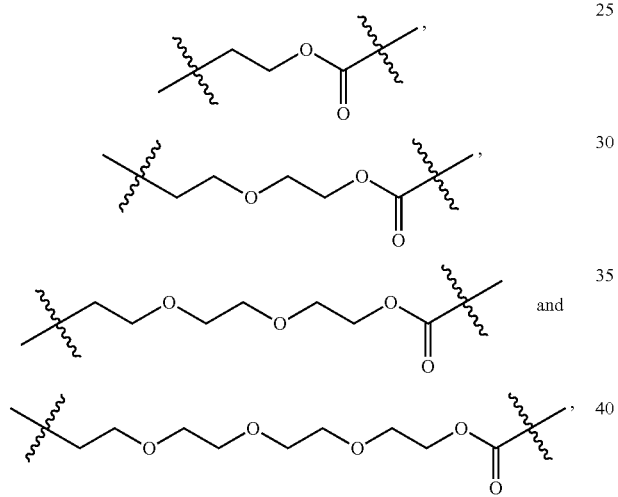
$V^1$ is a conditionally-cleavable dipeptide of natural and/or unnatural amino acids,
CL is a cyclization linker selected from
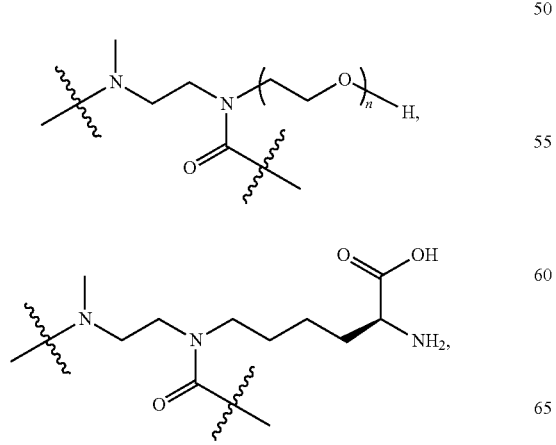
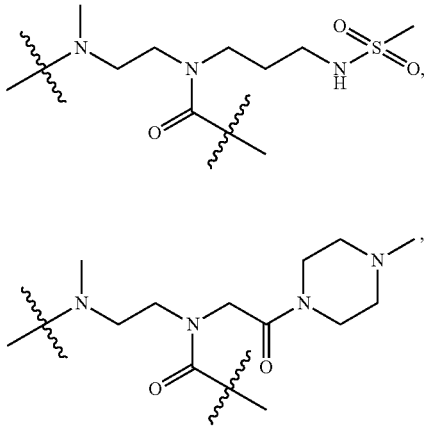
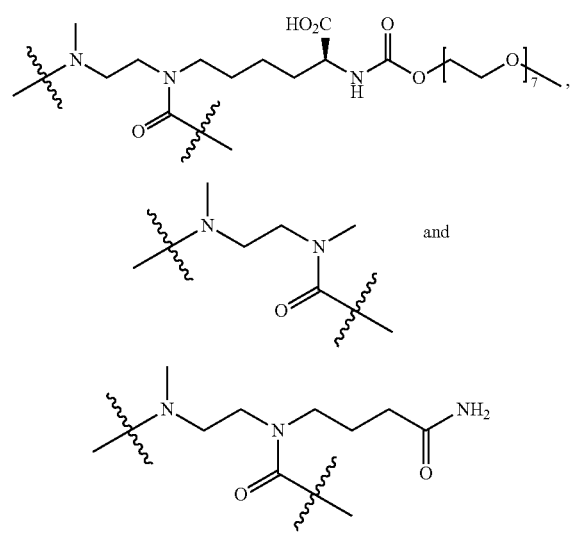
wherein n is an integer of from 1 to 16,
R is selected from H, $CH_3$, $CH_2CH_3$, $OCH_3$, $OCH_2CH_3$, $CF_3$, $OCF_3$, Cl, F,
q ranges from 0 to 8, and
DB is a DNA binding moiety selected from
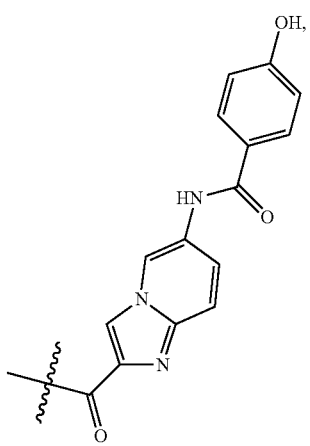

-continued

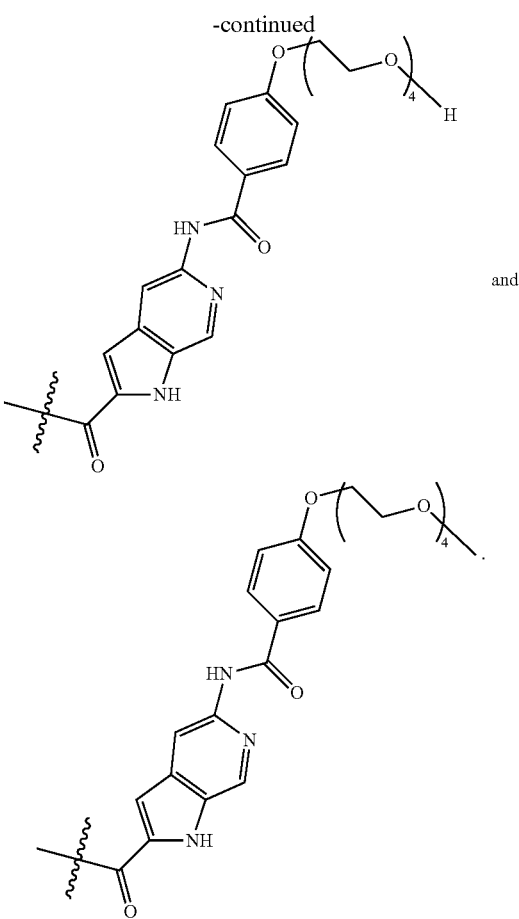

Such mixtures of Cys-linked ADCs have been described in detail in WO2010/062171 and WO2011/133039 of Applicant.

In accordance with the method of the present invention, the conditionally-cleavable dipeptide of natural and/or unnatural amino acids advantageously is selected from the group consisting of phenylalanyllysine, valyllysine, valylalanine, alanyllysine, valylcitrulline, N-methylvalylcitrulline, phenylalanylcitrulline, isoleucylcitrulline, tryptophanyllysine, tryptophanylcitrulline, phenylalanylarginine, phenylalanylalanine, phenylalanyl-N⁹-tosylarginine, phenylalanyl-N⁹-nitroarginine, leucyllysine, leucylcitrulline and phenylalanyl-O-benzoyl-threonine. Preferably, the dipeptide is phenylalanyllysine, valyllysine or valylcitrulline.

In accordance with the method of the present invention, the Ab is selected from the group consisting of an anti-CD19 antibody, an anti-CD22 antibody, an anti-CD30 antibody, an anti-CD33 antibody, an anti-CD56 antibody, an anti-CD70 antibody, an anti-CD74 antibody, an anti-CD138 antibody, an anti-CLL-1 antibody, an anti-5T4 antibody, an anti-CD303 antibody, an anti-Tag 72 antibody, an anti-Lewis A like carbohydrate antibody, an anti-EphB3 antibody, an anti-HMW-MAA antibody, an anti-CD38 antibody, an anti-Cripto antibody, an anti-EphA2 antibody, an anti-GPNMB antibody, an anti-integrin antibody, an anti-MN antibody, an anti-HER2 antibody, an anti-PSMA antibody, an anti-EGFR antibody, an anti-CD203c antibody, an anti-SLC44A4 antibody, an anti-Nectin-4 antibody, an anti-mesothelin antibody, an anti-CD44 antibody, an anti-CD79 antibody, an anti-FcRL5 antibody, an anti-MUC16 antibody, an anti-NaPi2b antibody, an anti-STEAP-1 antibody, an anti-ETBR antibody, an anti-TF antibody, an anti-MUC1 antibody, anti-HGFR antibody, an anti-CD37 antibody, an anti-FOLR1 antibody, an anti-CEACAM antibody, an anti-TROP2 antibody, an anti-GCC antibody, an anti-Lewis Y antibody, an anti-LIV1 antibody, an anti-DLL3 antibody, and an anti-EPCAM antibody. The antibody preferably is a monoclonal antibody (mAb).

In accordance with the method of the present invention, the Ab, or preferably mAb, is an anti-HER2 antibody. More preferably, the antibody is an anti-HER2 monoclonal antibody, particularly trastuzumab or a biosimilar thereof.

In a specific embodiment of the method of the present invention, a mixture of Cys-linked ADCs according to formula (II) is prepared by using the antibody trastuzumab or a biosimilar thereof, which antibody is reduced with tris(2-carboxyethyl)phosphine (TCEP, 1.1 molar equivalents per mole antibody) and is reacted with the linker-drug of formula (III) (1.3 molar equivalents per free thiol group). The conjugation typically is carried out in N,N-dimethylacetamide (DMAc) or dimethyl sulfoxide (DMSO), preferably in DMAc.

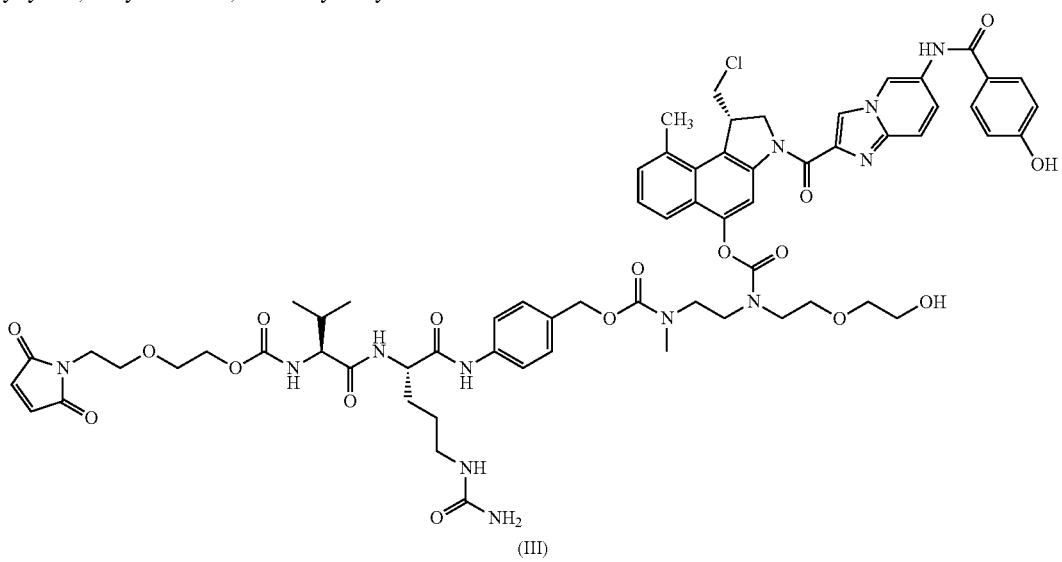

(III)

Ab = trastuzumab

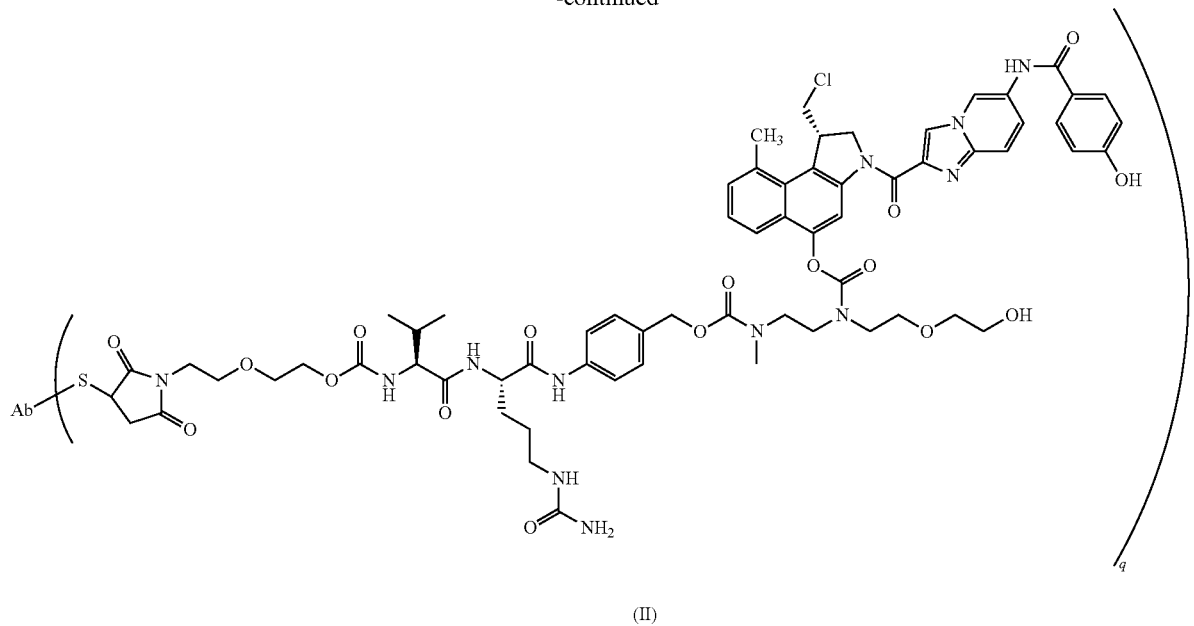

q = from 0 to 8

(II)

In certain embodiments of the method of the present invention, the conjugation reaction mixture is treated with an N-acetyl cysteine stock solution (1 molar equivalent per linker-drug conjugate) to block the reactive groups of non-conjugated linker-drug of formula (III).

In certain embodiments of the method of the present invention, the conjugation reaction mixture is subjected to a filtration step to remove insoluble excess of linker-drug of formula (III). Removing excess linker-drug before loading the reaction mixture onto the column increases the capacity of the column. Filters well known to those skilled in the art can be used. Typically, the filtration step involves use of a prefilter followed by a filter with an absolute pore size rating. Suitable prefilters are depth filters containing activated carbon. Preferred are filters such as ZetaCarbon SLP (3M).

Suitable absolute pore size filters are made of polyether sulphone (PES), cellulose acetate (CA) or polyvinylidene difluoride (PVDF). Preferred filters are PVDF or PES filters, typically with an absolute pore size of 0.2 μm.

In certain embodiments of the method of the present invention, the conjugation reaction mixture is prepared for HIC column purification by using sodium phosphate and ammonium sulphate, adjusted to a final concentration of 20-30 mM of sodium phosphate and 0.55-0.65 M ammonium sulphate at pH 6.0-6.5 (Buffer A).

In alternative embodiments of the method of the present invention, the conjugation reaction mixture is prepared for HIC column purification by using sodium acetate and ammonium sulphate, adjusted to a final concentration of 20-30 mM of sodium acetate and 0.55-0.9 M ammonium sulphate at pH 5.0-5.5 (Buffer A).

In a specific embodiment of the method of the present invention, the method involves the use of a HIC column (8 cm×20 cm, Butyl Sepharose 4 Fast Flow), which is first equilibrated with three column volumes of Buffer A (20-30 mM sodium phosphate, 0.55-0.65 M ammonium sulphate, pH 6.0-6.5) at a flow rate of 100 cm/h, followed by loading onto the column of the conjugation reaction mixture in Buffer A (step b) and collecting a flow-through fraction containing non-conjugated antibody (step c).

Step d involves washing the HIC column with three column volumes of the same Buffer A (20-30 mM sodium phosphate, 0.55-0.65 M ammonium sulphate, pH 6.0-6.5) at a flow rate of 100 cm/h while collecting the flow-through fraction, thereby removing the residual amounts of non-conjugated antibody.

Step e involves eluting the HIC column with three column volumes of Buffer B (20-30 mM sodium phosphate, 45-55 mM ammonium sulphate, pH 6.0-6.5) at a flow rate of 100 cm/h to obtain the purified mixture of Cys-linked ADCs. Said eluting can be performed either in a regular mode or in a reverse mode (as explained hereinabove).

In another specific embodiment of the method of the present invention, the method involves the use of a HIC column (1 cm×20 cm, Toyopearl PPG-600M), which is first equilibrated with three column volumes of Buffer A (20-30 mM sodium acetate, 0.55-0.9 M ammonium sulphate, pH 5.0-5.5) at a flow rate of 100 cm/h, followed by loading onto the column of the conjugation reaction mixture in Buffer A (step b) and collecting a flow-through fraction containing non-conjugated antibody (step c).

After loading, the HIC column is washed with three column volumes of the same Buffer A (20-30 mM sodium acetate, 0.55-0.9 M ammonium sulphate, pH 5.0-5.5) at a flow rate of 100 cm/h while collecting the flow-through fraction, thereby removing the residual amounts of non-conjugated antibody.

Step e involves eluting the HIC column with three column volumes of Buffer B (20-30 mM sodium acetate, pH 5.0-5.5) at a flow rate of 50-100 cm/h to obtain the purified mixture of Cys-linked ADCs. Said eluting can be performed either in a regular mode or in a reverse mode (as explained hereinabove).

As a result, the mixture of Cys-linked ADCs is purified to predominantly give the desired DAR2 and DAR4 species.

Under the above conditions, most of the DAR6 and DAR8 species, the non-conjugated linker-drug as well as any aggregate impurities remain on the HIC column. By washing the HIC column with water-for-injection (WFI) the DAR6 and DAR8 species as well as the non-conjugated linker-drug can be eluted from the column.

The method according to the present invention is particularly suitable for the purification of a mixture of cysteine-linked antibody-drug conjugates of the formula (II)

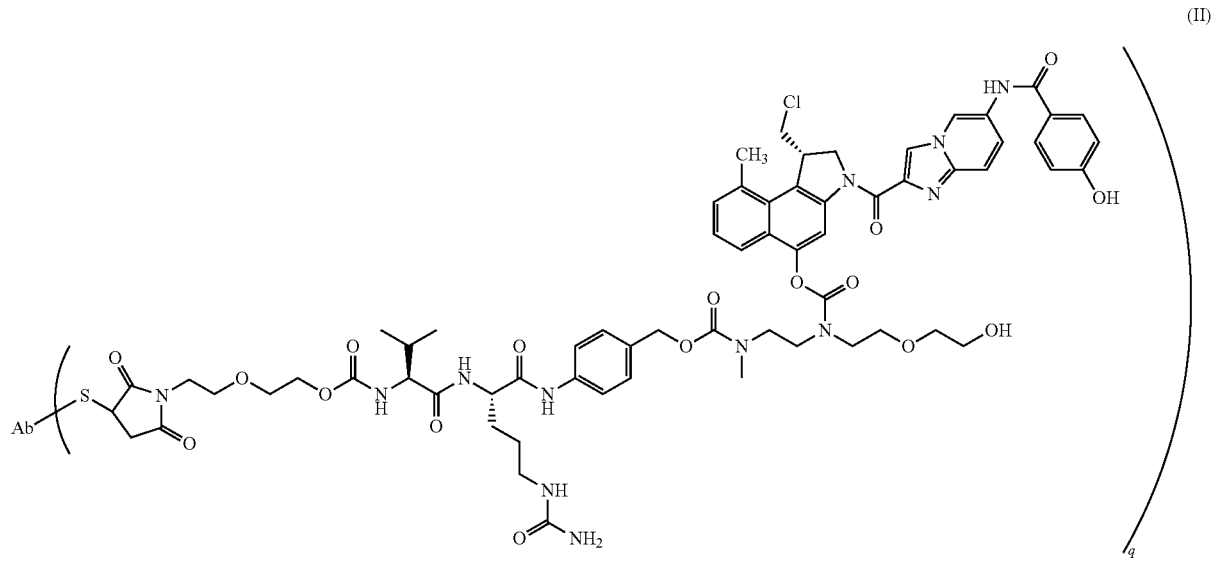

(II)

wherein

Ab is trastuzumab and q ranges from 0 to 8.

As a result of using the method for purifying a mixture of Cys-linked ADCs in accordance with the present invention, notably removing non-conjugated antibody from said mixture of ADCs, the average DAR increases. For example, as shown below in Example 3, the average DAR of a Cys-linked ADC compound according to formula (II) is increased from 1.75 to 2.5 after HIC purification.

After HIC purification, the buffer of the purified Cys-linked ADC typically is changed into a lyophilization buffer and subsequently the Cys-linked ADC is freeze-dried to give a lyophilized cake using conventional methods and equipment.

EXAMPLES

Example 1

Preparation of the Linker-drug Solution of Compound of Formula (III)

In the protective environment of an isolator (glove box), a sufficient amount of solid of the compound of formula (III) was weighed into a bottle. The solid was dissolved in 100% DMAc to a concentration of approx. 20 mM. Then, the bottle was taken out of the isolator and stored at room temperature, but protected from light, in a fume hood.

After determining the exact concentration, the linker-drug solution was diluted to 40 mM.

Example 2

Conjugation of Linker-drug with Trastuzumab

The anti-HER2 monoclonal antibody (mAb) trastuzumab was conjugated to the linker-drug of formula (III) giving a mixture of cysteine-linked antibody-drug conjugates of formula (II).

All handlings were performed under continuous stirring in a fume hood.

Immediately prior to conjugation, a solution of 60 mg/mL trastuzumab in 4.2 mM histidine, 50 mM trehalose, 0.01% polysorbate 20, pH 6 was mixed 2:1 with reduction buffer (4.2 mM histidine, 50 mM trehalose, 3 mM EDTA (ethylenediaminetetraacetic acid) and 1 mM TCEP, pH 6). TCEP is the reducing agent and is added in a molar ratio of 1.15 molar equivalents for 1 equivalent of trastuzumab to generate 2 free thiol groups per mAb. After incubation at room temperature for 60 min, N,N-dimethylacetamide (DMAc) solution (100%) and linker-drug of formula (III) (10 mM in DMAc, 2.2 equivalents with respect to mAb) were added such that the final concentration of DMAc was 2.5% v/v.

After overnight conjugation, the mixture was filtered through an activated carbon filter (ZetaCarbon SLP, 3M) followed by a 0.2 μm polyether sulfone (PES) filter to remove the insoluble excess of linker-drug of formula (III).

Figure 2:
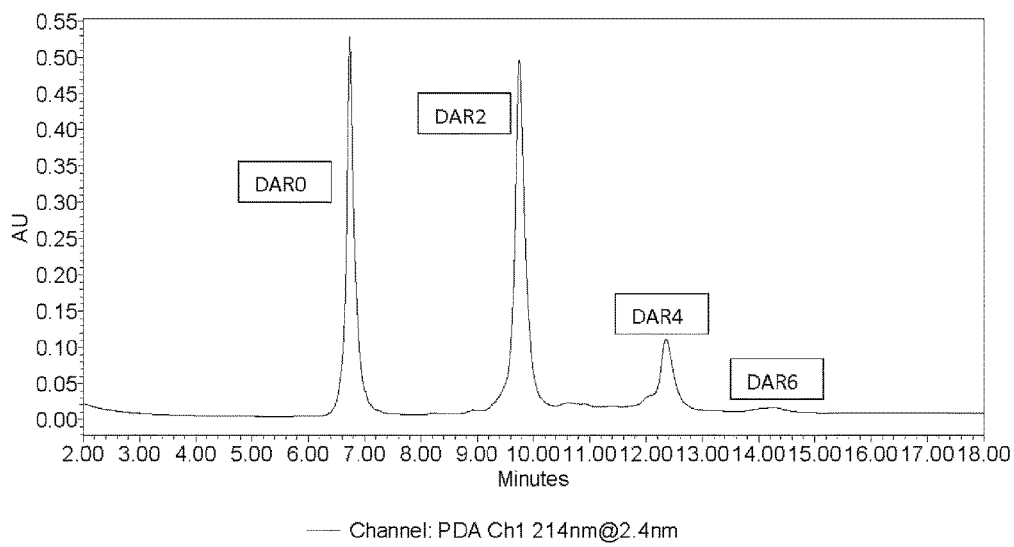
FIG. 2 depicts an analytical HIC chromatogram of a mixture of cysteine-linked antibody-drug conjugates according to formula (II) before and after HIC purification on a preparative scale according to the purification in Example 3.
Figure 2:
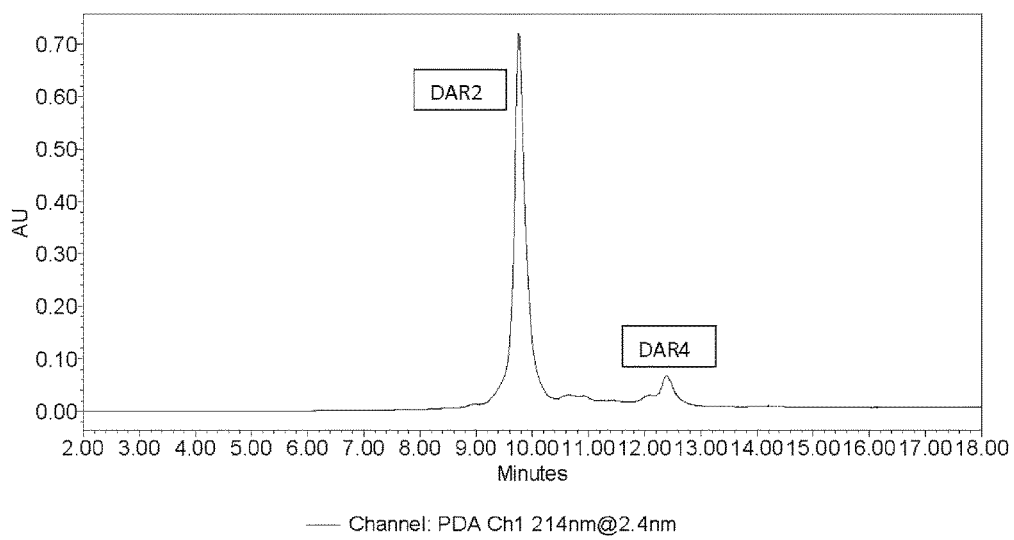
Figure 3:
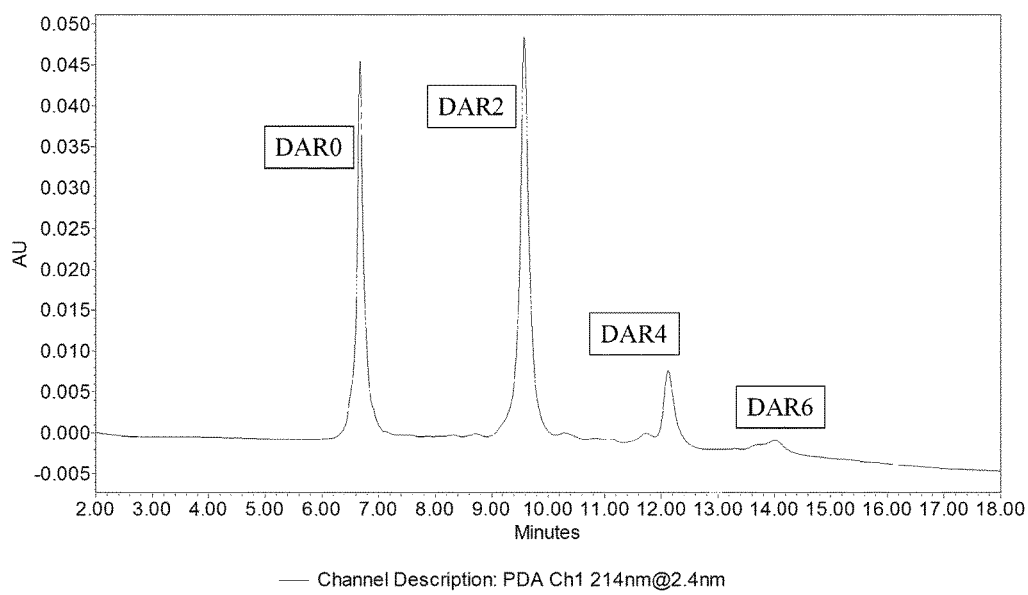
FIG. 3 depicts analytical HIC chromatograms of a mixture of cysteine-linked antibody-drug conjugates according to formula (II) before and after HIC purification on a preparative scale according to the purification in Example 4.
Figure 3:
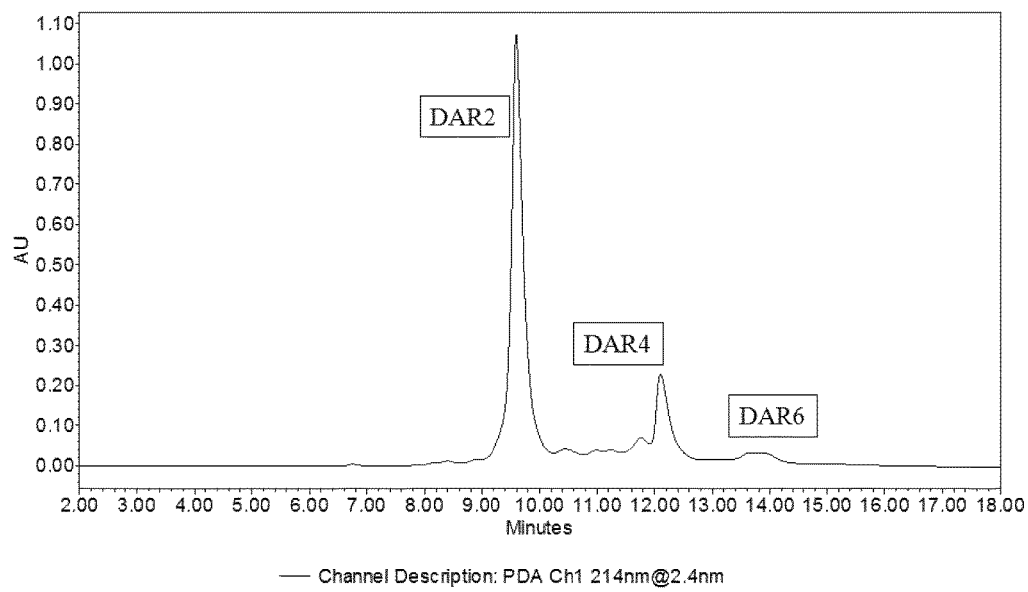

FIGS. 2A and 3A show the chromatogram of the obtained conjugation reaction mixture of two different batches on an analytical HIC column (described herein below). No DAR8 was detectable. The average DAR was calculated to be 1.75.

Example 3

Purification Using HIC

All chromatographic steps were performed at room temperature.

The conjugation reaction mixture obtained above was prepared for HIC column purification by mixing with a buffer of sodium phosphate (84 mM) and ammonium sulphate (2.21 M) in a ratio of 1 volume of buffer to 2 volumes of conjugation reaction mixture to a final concentration of sodium phosphate (26 mM) and ammonium sulphate (0.62 M) at pH 6.5. A preparative 8 cm×20 cm column was packed with Butyl Sepharose 4 Fast Flow (GE Healthcare). The column was equilibrated with 3 column volumes of Buffer A (26 mM sodium phosphate, 0.62 M ammonium sulphate, pH 6.5) at a flow rate of 100 cm/h. The conjugation reaction mixture was loaded onto the column up to 10 g/L column packing material/resin. The flow rate was set at 100 cm/h. Under these conditions, the non-conjugated antibody (i.e., trastuzumab) did not bind to the column/flowed through and was further washed off the column with 3 column volumes of Buffer A (26 mM sodium phosphate, 0.62 M ammonium sulphate, pH 6.5) at a flow rate of 100 cm/h. The flow-through fraction of loading and washing was collected and combined. Elution of the DAR2 and DAR4 species of cysteine-linked antibody-drug conjugates was realized by eluting with 3 column volumes of Buffer B (25 mM sodium phosphate, 50 mM ammonium sulphate, pH 6.2) at a flow rate of 100 cm/h. Under these conditions, any left non-conjugated linker-drug and most of the DAR6 cysteine-linked antibody-drug conjugates remained on the column. Washing the column with 2 column volumes of Water for Injection (WFI) at a flow rate of 100 cm/h eluted any left non-conjugated linker-drug and most of the DAR6 cysteine-linked antibody-drug conjugates.

FIG. 2B shows the chromatogram of the conjugation reaction mixture on an analytical HIC column (described herein below) after HIC purification on a preparative scale. No DAR0 was detectable. The average DAR was calculated to be 2.50.

Example 4

Alternative Purification Using HIC

All chromatographic steps were performed at room temperature.

A separate batch of a conjugation reaction mixture as obtained above was prepared for HIC column purification by mixing with a buffer of sodium acetate (75 mM) and ammonium sulphate (2.4 M) in a ratio of 1 volume of buffer to 2 volumes of conjugation reaction mixture to a final concentration of sodium acetate (25 mM) and ammonium sulphate (0.8 M) at pH 5.3.

A preparative 1 cm×20 cm column was packed with Toyopearl PPG-600M (Tosoh Bioscience). The column was equilibrated with 3 column volumes of Buffer A (25 mM sodium acetate, 0.8 M ammonium sulphate, pH 5.3) at a flow rate of 100 cm/h. The conjugation reaction mixture was loaded onto the column up to 35 g/L of column packing material/resin. The flow rate was set at 100 cm/h. Under these conditions, the non-conjugated antibody (i.e., trastuzumab) did not bind to the column/flowed through, and was further washed off the column with 3.5 column volumes of Buffer A (25 mM sodium acetate, 0.8 M ammonium sulphate, pH 5.3) at a flow rate of 100 cm/h. The flow-through fraction of loading and washing was collected and combined. Elution of the DAR2 and DAR4 species of cysteine-linked antibody-drug conjugates was realized by eluting with 3.5 column volumes of Buffer B (25 mM sodium acetate, pH 5.3) at a flow rate of 100 cm/h. Under these conditions, any left non-conjugated linker-drug and most of the DAR6 cysteine-linked antibody-drug conjugates remained on the column. Washing the column with 2 column volumes of 40% isopropanol at a flow rate of 100 cm/h eluted any left non-conjugated linker-drug and most of the DAR6 cysteine-linked antibody-drug conjugates.

FIG. 3B shows the chromatogram of the conjugation reaction mixture on an analytical HIC column (described herein below) after HIC purification on a preparative scale. No DAR0 was detectable. The average DAR was calculated to be 2.80.

Example 5

Analysis Using Analytical HIC

The analysis of cysteine-linked antibody-drug conjugates was performed by analytical hydrophobic interaction chromatography (HIC). The sample was prepared by diluting 10 µL of cysteine-linked antibody-drug conjugate with 90 µL 0.89 M aqueous ammonium sulphate solution resulting in a final concentration of 1 mg/mL of cysteine-linked antibody-drug conjugate in 0.8 M ammonium sulphate. 10 µL of the sample was injected onto a TSKgel Butyl-NPR column (Tosoh Bioscience). The elution method consisted of a linear gradient from 100% Buffer C (25 mM sodium phosphate, 1.5 M ammonium sulphate, pH 6.95) to 100% of Buffer D (25 mM sodium phosphate, pH 6.95, 20% isopropanol) at 0.4 ml/min over 20 minutes. A Waters Acquity H-Class UPLC system equipped with PDA-detector and Empower software was used. Absorbance was measured at 214 nm and the retention time of cysteine-linked antibody-drug conjugates was determined.

The same analytical method was applied on a sample of trastuzumab/Herceptin®, which sample was prepared as described above and of which sample the retention time was measured at 214 nm.

Example 6

Determination of Relative Hydrophobicity

The relative hydrophobicity of a DAR2 cysteine-linked antibody-drug conjugate species was calculated using the retention time (Rt) of said DAR2 species in the mixture of Cys-linked ADCs and the retention time of trastuzumab/Herceptin® using the following formula:

[Rt(DAR2)−Rt(trastuzumab/Herceptin®)]/Rt(trastuzumab/Herceptin®).

The DAR2 species of the cysteine-linked antibody-drug conjugate of formula (II) showed a retention time of 9.6 minutes and a relative hydrophobicity of 0.4 on the analytical HIC column described above, when the retention time of trastuzumab/Herceptin® was 6.7 minutes.

The invention claimed is:

1. A method for obtaining a purified mixture of cysteine-linked antibody-drug conjugates, which comprises:

a. providing a cysteine-linked antibody-drug conjugates mixture in a 0.2-1.5 M aqueous salt solution, wherein said mixture of cysteine-linked antibody-drug conjugates is of formula (I)

(I)
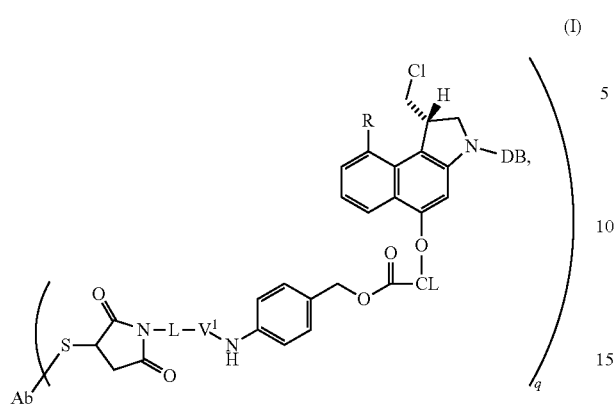
wherein
Ab is an antibody,
L is a linking group selected from
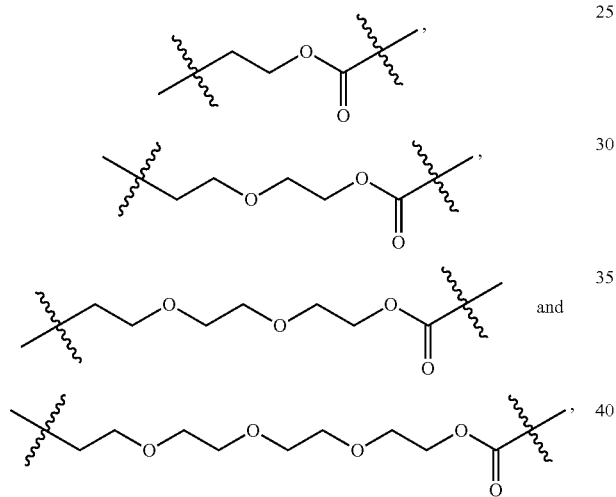
$V^1$ is a conditionally-cleavable dipeptide of natural and/or unnatural amino acids, CL is a cyclization linker selected from
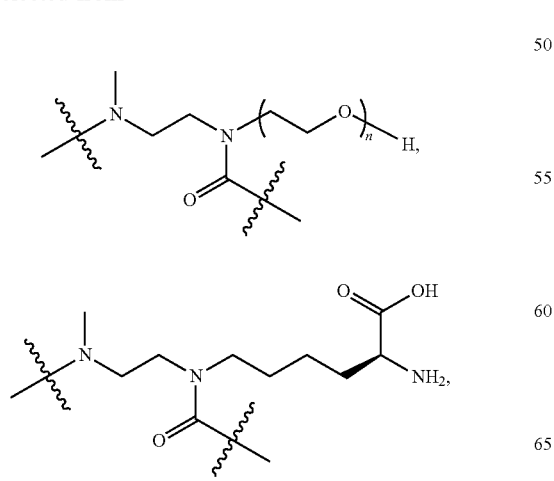
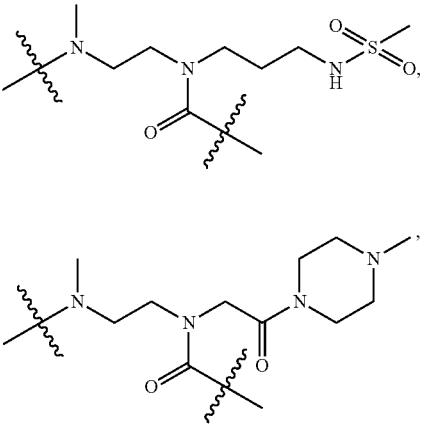
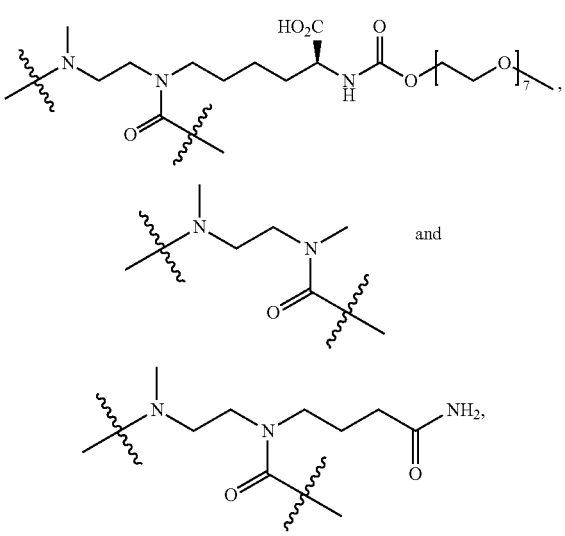
wherein n is an integer of from 1 to 16,
R is selected from H, $CH_3$, $CH_2CH_3$, $OCH_3$, $OCH_2CH_3$, $CF_3$, $OCF_3$, Cl, F,
q ranges from 0 to 8, and
DB is a DNA binding moiety selected from
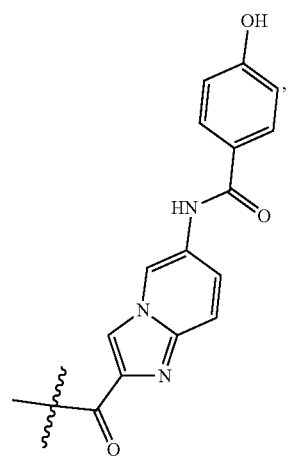

23
-continued
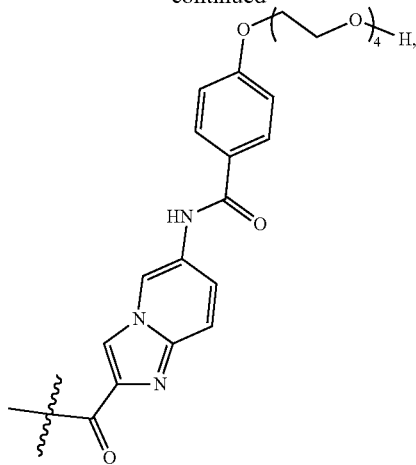
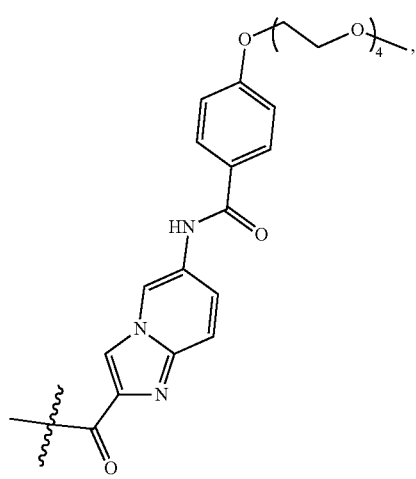
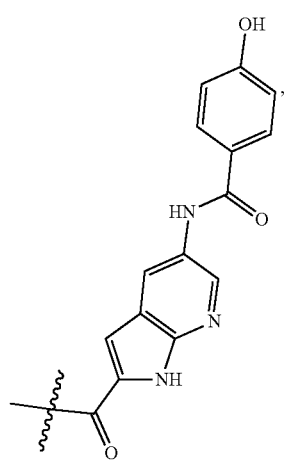
24
-continued
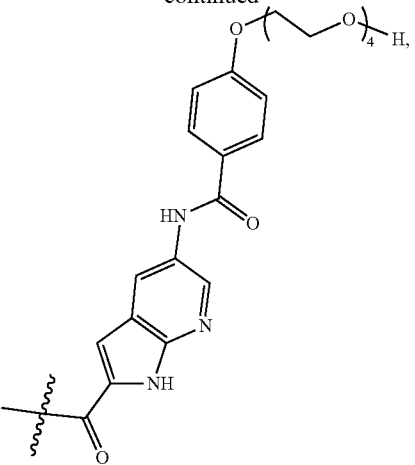
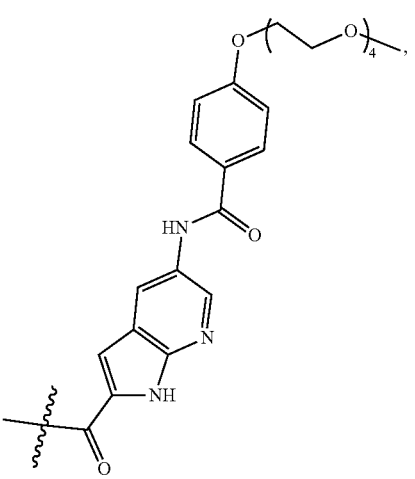
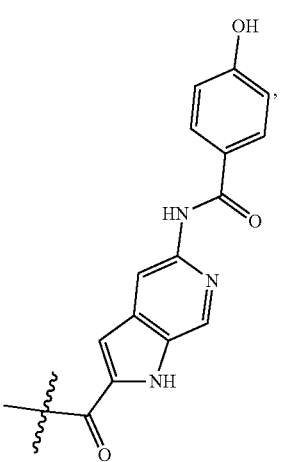

-continued

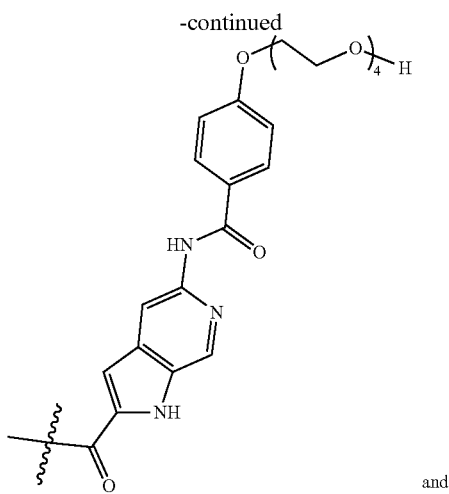

and

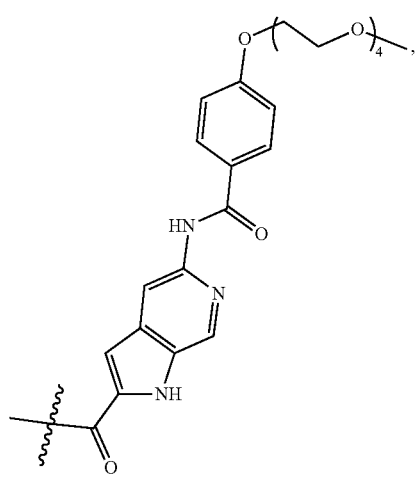

and wherein the amount of non-conjugated antibody in said mixture is in the range of 10-40% by weight;
b. loading said solution onto a preparative hydrophobic interaction chromatography column;
c. collecting a flow-through fraction that contains non-conjugated antibody;
d. washing said column with a 0.2-1.5 M aqueous salt solution while collecting the flow-through fraction; and
e. eluting said column with a 0-100 mM aqueous salt solution to obtain a purified mixture of cysteine-linked antibody-drug conjugates;
wherein no organic solvent is added in steps a, b, d, and e.

2. The method according to claim 1, wherein said column is packed with Fractogel EMD propyl, Fractrogel EMD phenyl, Butyl-S sepharose, Octyl Sepharose, Capto Octyl, Capto Butyl, Capto Phenyl ImpRes, Capto Butyl ImpRes, Toyopearl PPG-600M, Toyopearl Hexyl-650, Toyopearl Butyl-650, Toyopearl Phenyl-650, Toyopearl Ether-650, Macroprep t-Butyl, Macroprep phenyl, Cellufine Butyl, Cellufine Phenyl or Poros HP2.

3. The method according to claim 1, wherein said column has a diameter in the range of 4.0-2,000 mm.

4. The method according to claim 1, wherein the column loading is in the range of 5-50 g/L of column packing material.

5. The method according to claim 1, wherein the column contains column packing material that has an average particle size in the range of 30-180 μm.

6. The method according to claim 1, wherein the salt of the aqueous salt solution in each of steps (a), (d), and (e) is selected from the group consisting of potassium thiocyanate, sodium chloride, potassium chloride, ammonium chloride, sodium sulphate, potassium sulphate and ammonium sulphate.

7. The method according to claim 1, wherein the aqueous salt solution in each of steps (a), (d) and (e) further contains a buffer.

8. The method according to claim 7, wherein the buffer in each solution is selected from the group consisting of sodium phosphate, potassium phosphate, ammonium phosphate, sodium acetate, potassium acetate, sodium citrate, potassium citrate, ammonium citrate and mixtures thereof.

9. The method according to claim 7, wherein each of said aqueous salt solution is buffered to a pH of from about 4 to about 8.

10. The method according to claim 1, wherein the elution in step e is performed in a reverse mode.

11. The method according to claim 1, wherein the Ab is selected from the group consisting of an anti-CD19 antibody, an anti-CD22antibody, an anti-CD30 antibody, an anti-CD33 antibody, an anti-CD56 antibody, an anti-CD70 antibody, an anti-CD74 antibody, an anti-CD138 antibody, an anti-CLL-1 antibody, an anti-5T4 antibody, an anti-CD303 antibody, an anti-Tag 72antibody, an anti-Lewis A like carbohydrate antibody, an anti-EphB3 antibody, an anti-HMW-MAA antibody, an anti-CD38 antibody, an anti-Cripto antibody, an anti-EphA2 antibody, an anti-GPNMB antibody, an anti-integrin antibody, an anti-MN antibody, an anti-HER2 antibody, an anti-PSMA antibody, an anti-EGFR antibody, an anti-CD203c antibody, an anti-SLC44A4 antibody, an anti-Nectin-4antibody, an anti-mesothelin antibody, an anti-CD44 antibody, an anti-CD79antibody, an anti-FcRL5 antibody, an anti-MUC16 antibody, an anti-NaPi2b antibody, an anti-STEAP-1 antibody, an anti-ETBR antibody, an anti-TF antibody, an anti-MUC1 antibody, an anti-HGFR antibody, an anti-CD37 antibody, an anti-FOLR1 antibody, an anti-CEACAM antibody, an anti-TROP2 antibody, an anti-GCC antibody, an anti-Lewis Y antibody, an anti-LIV1 antibody, an anti-DLL3antibody, and an anti-EPCAM antibody.

12. The method according to claim 1, wherein the mixture of cysteine-linked antibody-drug conjugates of step (a) is of the formula (II)

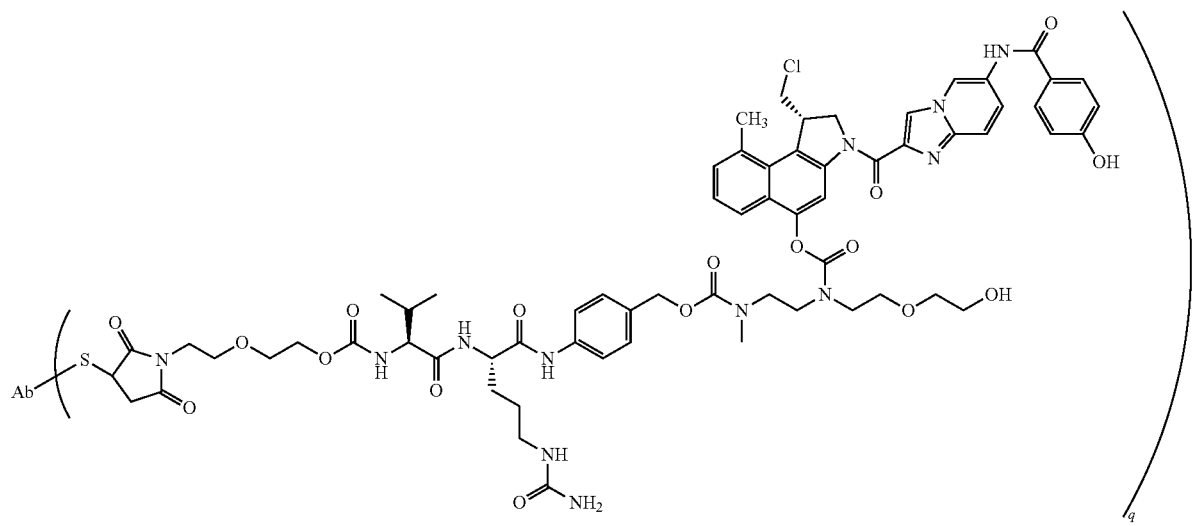

wherein
Ab is trastuzumab and
q ranges from 0 to 8.

13. The method according to claim 12, wherein the purified mixture of said cysteine-linked antibody-drug conjugates of the formula (II) has an average drug-to-antibody ratio (DAR) of from 2.6 to 2.9.

14. The method according to claim 13, wherein the average DAR is 2.80.

15. The method according to claim 3, wherein said column has a diameter in the range of 15-2,000 mm.

16. The method according to claim 4, wherein the column loading is in the range of 5-40 g/L of column packing material.

17. The method according to claim 6, wherein the salt is sodium chloride or ammonium sulphate.

18. The method according to claim 8, wherein the buffer is sodium phosphate or sodium acetate.

19. The method according to claim 13, wherein the average DAR is from 2.7 to 2.9.

20. The purified mixture of cysteine-linked antibody-drug conjugates as obtained according to claim 1.

21. The purified mixture according to claim 20, wherein the purified mixture of cysteine-linked antibody-drug conjugates has an average DAR of from 2.6 to 2.9.

22. The purified mixture according to claim 21, wherein the average DAR is from 2.7 to 2.9.

23. The purified mixture according to claim 22, wherein the average DAR is 2.80.

24. The purified mixture of cysteine-linked antibody-drug conjugates of the formula (II) as obtained according to claim 12.

25. The purified mixture according to claim 24, wherein the purified mixture of said cysteine-linked antibody-drug conjugates of the formula (II) has an average drug-to-antibody ratio (DAR) of from 2.6 to 2.9.

26. The purified mixture according to claim 25, wherein the average DAR is from 2.7 to 2.9.

27. The purified mixture according to claim 26, wherein the average DAR is 2.80.

28. The method according to claim 1, wherein said purified mixture of cysteine-linked antibody-drug conjugates has an average drug-to-antibody ratio of 2 to 3.

* * * * *